(12) United States Patent
Akao et al.

(10) Patent No.: US 12,022,881 B2
(45) Date of Patent: Jul. 2, 2024

(54) AEROSOL GENERATION DEVICE PROVIDED WITH CONTROL UNIT FOR DETECTION OF ABNORMAL STATE OF SENSOR

(71) Applicant: JAPAN TOBACCO INC., Tokyo (JP)

(72) Inventors: Takeshi Akao, Tokyo (JP); Manabu Yamada, Tokyo (JP); Hiroshi Tezuka, Tokyo (JP)

(73) Assignee: JAPAN TOBACCO INC., Tokyo (JP)

( * ) Notice: Subject to any disclaimer, the term of this patent is extended or adjusted under 35 U.S.C. 154(b) by 586 days.

(21) Appl. No.: 17/236,641

(22) Filed: Apr. 21, 2021

(65) Prior Publication Data
US 2021/0235768 A1 Aug. 5, 2021

Related U.S. Application Data

(63) Continuation of application No. PCT/JP2019/039606, filed on Oct. 8, 2019.

(30) Foreign Application Priority Data

Oct. 30, 2018 (JP) .................................. 2018-203939
Oct. 30, 2018 (JP) .................................. 2018-203940

(51) Int. Cl.
*A24F 40/50* (2020.01)
*A24F 40/10* (2020.01)
(Continued)

(52) U.S. Cl.
CPC .............. *A24F 40/53* (2020.01); *A24F 40/10* (2020.01); *A24F 40/51* (2020.01); *A24F 40/60* (2020.01);
(Continued)

(58) Field of Classification Search
CPC ................................. A24F 40/53; A24F 40/51
See application file for complete search history.

(56) References Cited

U.S. PATENT DOCUMENTS 9,877,510 B2    1/2018  Henry, Jr.
11,357,936 B2 * 6/2022  Lipowicz .......... A61M 15/0081
(Continued)

FOREIGN PATENT DOCUMENTS

JP          6022700 B2    11/2016
JP       2017-511690 A    4/2017
(Continued)

OTHER PUBLICATIONS

International Search Report (PCT/ISA/210) issued in PCT/JP2019/039606 dated Dec. 10, 2019.
(Continued)

*Primary Examiner* — Neil Abrams
(74) *Attorney, Agent, or Firm* — Birch, Stewart, Kolasch & Birch, LLP

(57) ABSTRACT

In order to detect the occurrence of malfunctions in a sensor, a power supply unit is provided with a suction action sensor which detects an aerosol generation request, and a control portion which, on the basis of an output value from the sensor which has detected an aerosol generation request, detects whether the sensor is in a normal state or an abnormal state. In one case, a control unit of the device may determine that the sensor is an abnormal state when the number of aerosol generation requests within a predetermined time period is greater than a predetermined threshold.

16 Claims, 14 Drawing Sheets

(51) Int. Cl.
*A24F 40/51* (2020.01)
*A24F 40/53* (2020.01)
*A24F 40/60* (2020.01)
*H01M 10/42* (2006.01)
*A61M 11/00* (2006.01)
*A61M 15/06* (2006.01)
*H02J 7/00* (2006.01)

(52) U.S. Cl.
CPC .......... *H01M 10/425* (2013.01); *A61M 11/00* (2013.01); *A61M 15/06* (2013.01); *A61M 2205/8206* (2013.01); *H01M 2010/4271* (2013.01); *H02J 7/0068* (2013.01)

(56) References Cited

U.S. PATENT DOCUMENTS

| | | | |
|---|---|---|---|
| 11,425,794 B2* | 8/2022 | Qiu | A24F 40/50 |
| 2011/0036346 A1* | 2/2011 | Cohen | A24F 40/60 |
| | | | 128/200.14 |
| 2015/0216233 A1 | 8/2015 | Sears et al. | |
| 2016/0128389 A1 | 5/2016 | Lamb et al. | |
| 2016/0205998 A1 | 7/2016 | Matsumoto et al. | |
| 2019/0124989 A1 | 5/2019 | Qiu | |
| 2021/0235768 A1* | 8/2021 | Akao | A24F 40/53 |
| 2022/0260399 A1* | 8/2022 | Arwatz | A24F 40/51 |
| 2022/0408833 A1* | 12/2022 | Lee | A24F 40/95 |

FOREIGN PATENT DOCUMENTS

| | | |
|---|---|---|
| JP | 2017-512480 A | 5/2017 |
| JP | 2017-535265 A | 11/2017 |
| WO | WO 2018/032951 A1 | 2/2018 |

OTHER PUBLICATIONS

Extended European Search Report for European Application No. 19879687.2, dated Jul. 8, 2022.

* cited by examiner

Fig. 21

| CONTENT OR CAUSE OF TROUBLE IN MICROPHONE CAPACITOR 331 | OPERATING CONTENT OF NOTIFICATION UNIT 360 |
|---|---|
| VOLTAGE VALUE APPLIED TO PTC THERMISTOR 332 IS EQUAL TO OR HIGHER THAN THRESHOLD VOLTAGE | BLINK FOUR TIMES ALTERNATELY IN RED AND BLUE |
| INTERVAL t1 BETWEEN SUCTION ACTIONS IS EQUAL TO OR LESS THAN THRESHOLD TIME PERIOD T1 | BLINK SIX TIMES ALTERNATELY IN RED AND BLUE |
| DURATION t2 OF ONE SUCTION ACTION IS EQUAL TO OR LESS THAN THRESHOLD TIME PERIOD T2a | BLINK EIGHT TIMES ALTERNATELY IN RED AND BLUE |
| INTEGRATED HEATING TIME PERIOD t3 WITHIN PREDETERMINED TIME PERIOD Ta IS EQUAL TO OR GREATER THAN THRESHOLD TIME PERIOD T3 | BLINK 10 TIMES ALTERNATELY IN RED AND BLUE |
| THE NUMBER OF TIMES THAT SUCTION ACTION HAS BEEN DETECTED WITHIN PREDETERMINED TIME PERIOD Tb IS EQUAL TO OR GREATER THAN n TIMES | BLINK 12 TIMES ALTERNATELY IN RED AND BLUE |

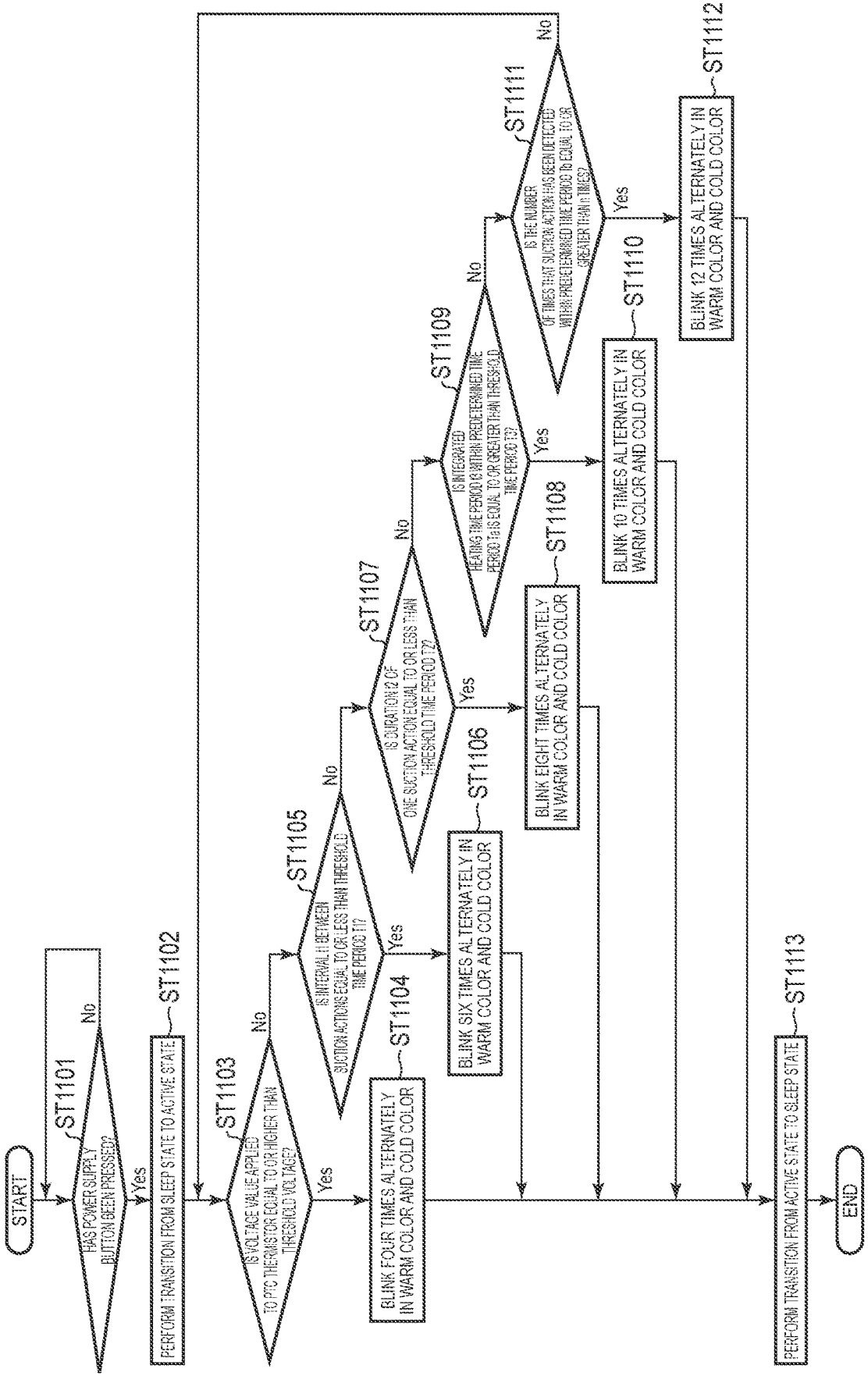

AEROSOL GENERATION DEVICE PROVIDED WITH CONTROL UNIT FOR DETECTION OF ABNORMAL STATE OF SENSOR

CROSS REFERENCE TO RELATED APPLICATIONS

This application is a Continuation of PCT International Application No. PCT/JP2019/039606, filed on Oct. 8, 2019, which claims priority under 35 U.S.C. 119(a) to Patent Application Nos. 2018-203939 and 2018-203940, filed in Japan on Oct. 30, 2018, all of which are hereby expressly incorporated by reference into the present application.

TECHNICAL FIELD

The present invention relates to a power supply unit of an aerosol generation device, a control method for the power supply unit of the aerosol generation device, and a program for the power supply unit of the aerosol generation device.

BACKGROUND ART

An aerosol generation device is known with which a user can taste aerosol generated by atomizing an aerosol source with an electric load such as a heater.

PTL 1 discloses a technique of supplying electric power to a heater when a user's suction action is detected based on an output of a sensor that measures an amount of air flowing in the device.

PTL 2 discloses a technique of adjusting a value of electric power to be supplied to a heater based on an output of a sensor that measures a flow rate of air flowing in the device.

As a technique related to the aerosol generation device, a technique of notifying that a user's suction action has started or a remaining amount of the battery has decreased, using a light emitting diode (LED).

PTL 3 discloses a technique of causing a light-emitting element to emit light in different modes between a case where a user's suction action is performed and a case where a user's suction action is not performed.

PTL 4 discloses a technique of adjusting light intensity of an illumination source based on an internal temperature of a heating element or the like.

CITATION LIST

Patent Literature

PTL 1: Japanese Translation of PCT International Application Publication No. 2017-535265
PTL 2: Japanese Translation of PCT International Application Publication No. 2017-512480
PTL 3: Japanese Patent No. 6022700
PTL 4: Japanese Translation of PCT International Application Publication No. 2017-511690

SUMMARY OF INVENTION

Technical Problem

When the aerosol generation device continues to be used, a sensor that detects a user's suction action may have a trouble due to deterioration over time and the like. When the sensor has such a trouble, the aerosol source is atomized by the aerosol generation device without user's intention, for example, when the user does not perform the suction action, whereby the aerosol source may be wasted. Therefore, in the case where the trouble has occurred in the sensor, it is desired to detect such occurrence of trouble.

However, the techniques disclosed in PTLs 1 and 2 are techniques of controlling the supply of electric power to the heater according to an output value of the sensor, and do not reflect detecting the trouble in the sensor.

The present invention has been made in view of the above circumstances, and has a first object to provide a power supply unit of an aerosol generation device capable of detecting occurrence of a trouble in a sensor, a control method for the power supply unit of the aerosol generation device, and a program for the power supply unit of the aerosol generation device.

To perform repairs to solve such a trouble, it is necessary to recognize the content or cause of the trouble. To recognize the content or cause of the trouble, various inspections are required to be performed, which may take a lot of time and labor. Therefore, there is desired a technique capable of easily recognizing the content or cause of the trouble.

However, the technique disclosed in PTL 3 is a technique of causing an LED to emit light in different modes based on a user's suction action. The technique disclosed in PTL 4 is a technique of adjusting light intensity of an illumination source based on an internal temperature of a heating element or the like. These techniques do not reflect recognizing a content or cause of a trouble that has occurred in a sensor.

The present invention has been made in view of the above circumstances, and has a second object to provide a power supply unit of an aerosol generation device capable of easily recognizing a content or a cause of a trouble that has occurred in a sensor, a control method for the power supply unit of the aerosol generation device, and a program for the power supply unit of the aerosol generation device.

Solution to Problem

A power supply unit of an aerosol generation device according to a first embodiment of the present invention includes a sensor that detects an aerosol generation request while the power supply unit is in an active state, and a control unit that determines whether the sensor is in a normal state or an abnormal state based on an output value from the sensor that has detected the aerosol generation request, wherein the control unit causes the power supply unit to undergo a transition to a sleep state that allows the power supply unit to undergo a transition to the active state again, when detecting the abnormal state.

In addition, the control unit is capable of causing the power supply unit to undergo the transition from the sleep state to the active state again when the detected abnormal state is caused by leakage of an aerosol source.

An output value from the sensor when the control unit determines that the sensor is in the normal state can be different from an output value from the sensor when the control unit determines that the sensor is in the abnormal state.

The output value from the sensor when the control unit determines that the sensor is in the abnormal state may be a value that is not due to an aerosol generation request from a user of the aerosol generation device.

The output value from the sensor when the control unit determines that the sensor is in the abnormal state may be a value that is due to an aerosol generation request caused and detected by the sensor itself.

The abnormal state may be a state of the sensor in a case where an aerosol source is not atomized by an atomization unit that receives supply of electric power from the power supply unit or in a case where the atomization unit atomizes the aerosol source so that the aerosol source held by a supply unit that supplies the aerosol source to the atomization unit is depleted.

The normal state may be a state of the sensor in a case where an atomization unit that receives supply of electric power from the power supply unit atomizes an aerosol source so that the aerosol source held by a supply unit that supplies the aerosol source to the atomization unit is not depleted.

The control unit may be configured to determine that the sensor is in the abnormal state when a time interval from when the sensor detects a certain aerosol generation request to when the sensor detects a next aerosol generation request is equal to or less than a predetermined threshold.

The control unit may be configured to determine that the sensor is in the abnormal state when duration of an aerosol generation request detected by the sensor is equal to or less than a predetermined threshold.

The control unit may be configured to determine that the sensor is in the abnormal state when a total time period for which the sensor detects an aerosol generation request within a predetermined time period is equal to or greater than a predetermined threshold.

The control unit may be configured to determine that the sensor is in the abnormal state when the number of times that the sensor has detected an aerosol generation request within a predetermined time period is equal to or greater than a predetermined threshold.

The power supply unit further includes a notification unit, and when determining that the sensor is in the abnormal state, the control unit may be configured to cause the notification unit to make a notification that the sensor is in the abnormal state.

The power supply unit further includes a memory unit, and the memory unit may be configured to store information indicating the number of times that the control unit has detected the abnormal state.

The memory unit may be configured to further store information indicating a content of the abnormal state detected by the control unit.

When detecting an instruction to cause the power supply unit to undergo a transition to an active state, the control unit may be configured not to cause the power supply unit to undergo the transition to the active state when the number of times that the control unit has detected the abnormal state is equal to or greater than a predetermined threshold, or configured to cause the power supply unit to undergo the transition to the active state when the number of times is less than the predetermined threshold.

The control unit may be configured to perform a process of detecting whether the sensor is in the normal state or the abnormal state while the power supply unit is in the active state.

A control method for a power supply unit of an aerosol generation device according to the first embodiment of the present invention includes the steps of determining whether a sensor is in a normal state or an abnormal state based on an output value from the sensor that has detected an aerosol generation request while the power supply unit is in an active state, and causing the power supply unit to undergo a transition to a sleep state that allows the power supply unit to undergo a transition to the active state again, when detecting the abnormal state.

A program for a power supply unit of an aerosol generation device according to the first embodiment of the present invention causes a computer to execute processes of determining whether a sensor is in a normal state or an abnormal state based on an output value from the sensor that has detected an aerosol generation request while the power supply unit is in an active state, and causing the power supply unit to undergo a transition to a sleep state that allows the power supply unit to undergo a transition to the active state again, when detecting the abnormal state.

A power supply unit of an aerosol generation device that supplies electric power to a load that generates aerosol, according to a second embodiment of the present invention, includes a sensor that is in an operating state among a normal state and a plurality of abnormal states, and detects an aerosol generation request while the power supply unit is in an active state, a control unit that detects a state of the sensor, and generates an error signal capable of distinguishing between a first and second abnormal states when the sensor is in at least one of the first and second abnormal states included in the plurality of abnormal states, and a notification unit that makes a notification in a different mode for each type of the error signal. The control unit causes the power supply unit to undergo a transition from the active state to a sleep state after generating the error signal. The plurality of abnormal states include a state in which supply of electric power to the load is unnecessary for detection by the control unit.

The plurality of abnormal states may include a state in which supply of electric power to the load is necessary for detection by the control unit.

The abnormal state of the sensor may be classified into n states (n is a natural number of 2 or more). The number of types of the error signals capable of being generated by the control unit may be n at a maximum.

The control unit may generate an error signal whose type varies according to the state of the sensor.

When the error signal is generated and when the sensor detects the aerosol generation request after the error signal is generated, the control unit may cause the notification unit to make a notification in a mode based on the generated error signal.

When the error signal is generated and when the sensor detects a predetermined operation that does not involve the sensor after the error signal is generated, the control unit may cause the notification unit to make a notification in a mode based on the generated error signal.

The predetermined operation may be an operation in which an instruction to cause the aerosol generation device to undergo a transition to an active state is issued predetermined times.

The abnormal state may include a state when a voltage applied to other elements that changes based on an electric state of the sensor is equal to or greater than a predetermined threshold.

The abnormal state may include a state when a time interval from when the sensor detects a certain aerosol generation request to when the sensor detects a next aerosol generation request is equal to or less than a predetermined threshold.

The abnormal state may include a state when duration of an aerosol generation request detected by the sensor is equal to or less than a predetermined threshold.

The abnormal state may include a state when a total time period for which the sensor detects an aerosol generation request within a predetermined time period is equal to or greater than a predetermined threshold.

The abnormal state may include a state when the number of times that the sensor has detected an aerosol generation request within a predetermined time period is equal to or greater than a predetermined threshold.

The control unit may cause the notification unit to emit light in a different mode for each type of the error signal.

The control unit may cause the notification unit to generate a vibration in a different mode for each type of the error signal.

The control unit may cause the notification unit to emit a sound in a different mode for each type of the error signal.

Importance may be set for each type of the error signal. The control unit may cause the notification unit to make a notification in a higher power consumption mode regarding the notification based on an error signal for which the importance is set higher.

The abnormal state may be a state in which the sensor undergoes a transition in a case where an aerosol source is not atomized by a load that receives supply of electric power from the power supply unit or in a case where the load atomizes the aerosol source so that the aerosol source held by a supply unit that supplies the aerosol source to the load is depleted.

The normal state may be a state in which the sensor undergoes a transition in a case where a load that receives supply of electric power from the power supply unit atomizes an aerosol source so that the aerosol source held by a supply unit that supplies the aerosol source to the load is not depleted.

A control method for a power supply unit of an aerosol generation device that supplies electric power to a load that generates aerosol, according to a second embodiment of the present invention, includes the steps of causing a sensor that is in an operating state among a normal state and a plurality of abnormal states to detect an aerosol generation request while the power supply unit is in an active state, generating an error signal capable of distinguishing between a first and second abnormal states when the sensor is in at least one of the first and second abnormal states included in the plurality of abnormal states, making a notification in a different mode for each type of the error signal, and causing the power supply unit to undergo a transition from the active state to a sleep state after generating the error signal. The plurality of abnormal states include a state in which supply of electric power to the load is unnecessary for detection by the control unit.

The plurality of abnormal states may include a state in which supply of electric power to the load is necessary for detection by the control unit.

A program for a power supply unit of an aerosol generation device according to a second embodiment of the present invention causes a computer for the power supply unit of an aerosol generation device that supplies electric power to a load that generates aerosol to execute processes of causing a sensor that is in an operating state among a normal state and a plurality of abnormal states to detect an aerosol generation request while the power supply unit is in an active state, generating an error signal capable of distinguishing between a first and second abnormal states when the sensor is in at least one of the first and second abnormal states included in the plurality of abnormal states, making a notification in a different mode for each type of the error signal, and causing the power supply unit to undergo a transition from the active state to a sleep state after generating the error signal. The plurality of abnormal states include a state in which supply of electric power to the load is unnecessary for detection by the control unit.

The plurality of abnormal states may include a state in which supply of electric power to the load is necessary for detection by the control unit.

Advantageous Effects of Invention

According to a power supply unit of an aerosol generation device according to a first embodiment of the present invention, a control method for the power supply unit of the aerosol generation device, and a program for the power supply unit of the aerosol generation device, the occurrence of a trouble in a sensor can be detected.

According to a power supply unit of an aerosol generation device according to a second embodiment of the present invention, a control method for the power supply unit of the aerosol generation device, a program for the power supply unit of the aerosol generation device, a content or a cause of a trouble that has occurred in a sensor can be easily recognized.

BRIEF DESCRIPTION OF DRAWINGS

FIG. 21 is a table showing an example of control information according to the second embodiment of the present invention.

FIG. 22 is a flowchart illustrating an example of an operation of the aerosol generation device according to the second embodiment of the present invention.

DESCRIPTION OF EMBODIMENTS

Hereinafter, embodiments of the present invention will be described with reference to the drawings. Note that in the following description, approximately or substantially the same functions and constituent elements are denoted by the same reference signs, and are described only when necessary.

First Embodiment

In the following description, it is assumed that an aerosol generation device 1 according to the present embodiment is, for example, a heated cigarette or an electronic cigarette. However, the aerosol generation device 1 according to the present embodiment may be an aerosol generation device of another type or usage, such as a nebulizer.

Figure 1:
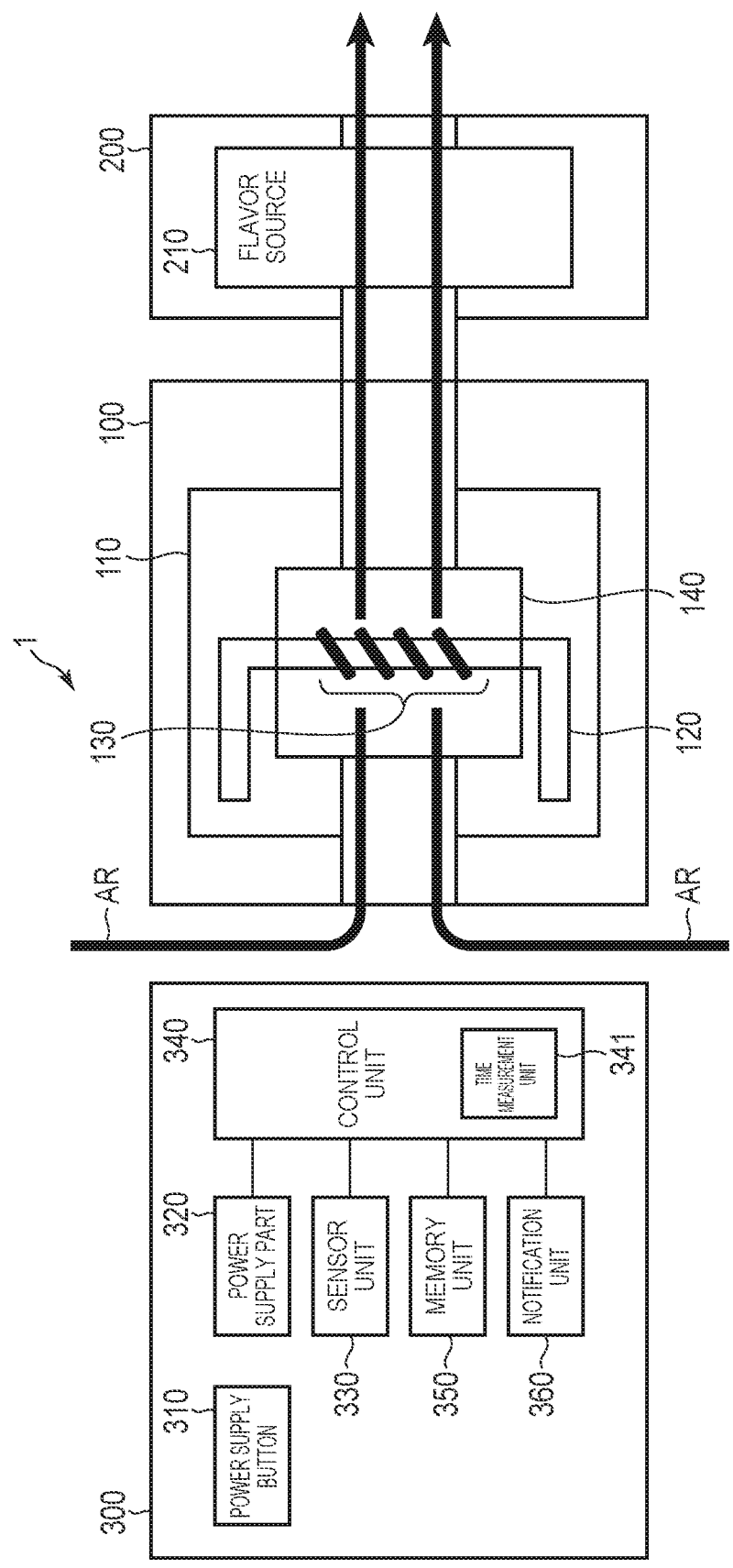
FIG. 1 is a block diagram illustrating an example of a schematic configuration of an aerosol generation device according to a first embodiment of the present invention.

FIG. 1 is a block diagram illustrating an example of a schematic configuration of the aerosol generation device 1 according to the present embodiment.

As illustrated in FIG. 1, the aerosol generation device 1 includes a cartridge unit 100, a capsule unit 200, and a power supply unit 300. The aerosol generation device 1 is configured, for example, in a substantially cylindrical shape, so that a user can easily hold the aerosol generation device 1. Note that the cartridge unit 100, the capsule unit 200, and the power supply unit 300 may be configured to be connected to one another in a non-detachable or detachable manner.

As illustrated in FIG. 1, the cartridge unit 100 includes a storage unit 110, a supply unit 120, and an atomization unit 140 provided with a load 130.

The storage unit 110 is a container for storing a liquid aerosol source to be atomized through heating. The aerosol source is, for example, a polyol-based material such as glycerin or propylene glycol. The aerosol source may also be a liquid mixture that contains a nicotine liquid, water, a flavoring agent, etc. Alternatively, the aerosol source may also be a solid for which the storage unit 110 is unnecessary.

The supply unit 120 is, for example, a wick that is formed by twisting a fiber material such as glass fibers. One end of the supply unit 120 is connected to the storage unit 110. The other end of the supply unit 120 is connected to the load 130 or is arranged in the vicinity of the load 130. With such an arrangement, the supply unit 120 can soak up the aerosol source from the storage unit 110 and guide the aerosol source to the load 130 or the vicinity of the load 130. Note that the wick made of porous ceramic may also be used for the supply unit 120.

The load 130 provided in the atomization unit 140 is a coil-shaped heater, for example, and generates heat when the electric power is supplied thereto. The load 130 may be wound around the supply unit 120 or may be covered by the supply unit 120. The electric power is supplied to the load 130 from a power supply part 320, which will be described later, based on the control by a control unit 340, which will be described later, included in the power supply unit 300. When the electric power is supplied to the load 130, the aerosol source guided by the supply unit 120 is heated by the load 130, whereby aerosol is generated.

The capsule unit 200 includes a flavor source 210, as illustrated in FIG. 1.

The flavor source 210 includes a raw material piece of a plant material that imparts a flavor component to the aerosol. For example, shredded tobacco or a forming body obtained by forming a tobacco material such as a tobacco raw material in a granular form or a sheet form is used as the raw material piece which is a component of the flavor source. In addition, a plant (for example, mint, a herb, or the like) other than tobacco may be used as the raw material piece which is a component of the flavor source 210. The flavor source 210 may be provided with a flavor such as menthol.

Each arrow in FIG. 1 indicates the flow of air in the cartridge unit 100 and the capsule unit 200. The air taken in from the outside through an air intake opening (not illustrated) is mixed with the aerosol in the process of passing through the aerosol generation device 1 (the cartridge unit 100 and the capsule unit 200) to which a flavor component is added, and the resultant mixture is sucked by the user. Specifically, the air taken in from the outside passes through the atomization unit 140 in the cartridge unit 100. While passing through the atomization unit 140, the air is mixed with the aerosol generated by the load 130 provided in the atomization unit 140. Then, when the air mixed with the aerosol passes through the capsule unit 200, the flavor component derived from the flavor source 210 included in the capsule unit 200 is added to the air mixed with the aerosol. Then, the air mixed with the aerosol and added with the flavor component is sucked by the user from the end portion of the capsule unit 200. That is, the aerosol to which the flavor component is added is sucked by the user.

As illustrated in FIG. 1, the power supply unit 300 includes a power supply button 310, the power supply part 320, a sensor unit 330, the control unit 340 provided with a time measurement unit 341, a memory unit 350, and a notification unit 360.

The power supply button 310 is a button for causing an operating state transition of the aerosol generation device 1. When the power supply button 310 is pressed to turn on the power supply, the aerosol generation device 1 undergoes the transition to an active state, which will be described later. When the power supply button 310 is pressed to turn off the power supply while the aerosol generation device 1 is in the active state, the aerosol generation device 1 undergoes the transition from the active state to a sleep state, which will be described later.

Note that saying that the aerosol generation device 1 is in the active state is equivalent to saying that the battery unit 300 is in the active state. Moreover, saying that the aerosol generation device 1 is in the sleep state is equivalent to saying that the battery unit 300 is in the sleep state.

The power supply part 320 is, for example, a rechargeable battery such as a lithium-ion secondary battery, and its type is not limited. The power supply part 320 supplies the electric power to each portion of the aerosol generation device 1 based on the control by the control unit 340.

The sensor unit 330 is a sensor that outputs a predetermined output value (for example, a voltage value or a current value) to the control unit 340 according to, for example, the flow rate and/or the flow velocity of gas passing through the sensor unit 330. Such a sensor unit 330 is used to detect a user's suction action (an action for requesting the aerosol generation device 1 to generate the aerosol). Although various types of sensors can be used as the sensor unit 330, for example, a microphone capacitor, or the like is used.

Here, the microphone capacitor is a sensor including a diaphragm that is a metal plate made to vibrate by changes in sound and pressure due to the user's suction action, and a back plate is a fixed metal plate. The user's suction action is detected by the control unit 340 based on a change in an electrostatic capacitance defined by the diaphragm and the back plate.

Specifically, since the diaphragm does not vibrate when there are no changes in sound and pressure due to the user's suction action, the electrostatic capacitance defined by the diaphragm and the back plate does not change. On the other hand, when there are changes in sound and pressure due to the user's suction action, the diaphragm vibrates based on the changes in sound and pressure, and the electrostatic capacitance defined by the diaphragm and the back plate changes. Therefore, the user's suction action is detected based on the change in the electrostatic capacitance.

The control unit 340 causes the aerosol generation device 1 to undergo the transition to one of two operating states when the power supply button 310 is pressed. The two operating states include an active state in which the electric power can be supplied from the power supply part 320 to each portion of the aerosol generation device 1 and a sleep state in which no electric power can be supplied from the power supply part 320 to each portion of the aerosol generation device 1 or only minimal electric power can be supplied from the power supply part 320 to each portion of the aerosol generation device 1. When the sensor unit 330 detects the user's suction action while the aerosol generation device 1 is in the active state, the control unit 340 causes the power supply part 320 to supply the electric power to the load 130 to atomize the aerosol source. When the power supply unit 300 is in the sleep state, the control unit 340 does not cause the power supply part 320 to supply the electric power to the load 130 even when the user performs a suction action. Therefore, the aerosol source is not atomized. Note that the electric power is continuously supplied from the power supply part 320 to the load 130 under the control by the control unit 340 while the sensor unit 330 detects the user's suction action.

The control unit 340 detects whether the sensor unit 330 is in the normal state or the abnormal state, based on the output from the sensor unit 330 and the output from the time measurement unit 341 that measures various times such as a start time of the user's suction action. Note that the time measurement unit 341 is a meter that can measure the time, such as a clock, or a stopwatch, for example, and its type is not limited.

Here, the normal state refers to a state in which the sensor unit 330 has no trouble and can normally detect the user's suction action. In other words, the normal state refers to a state in which when the user performs the suction action, the sensor unit 330 detects such a suction action, and the electric power is supplied to the load 130, whereby the aerosol is generated.

The abnormal state refers to a state in which the sensor unit 330 has a trouble, and cannot normally detect the user's suction action. Here, the following four examples are examples in which the control unit 340 detects that the sensor unit 330 is in the abnormal state.

Figure 2:
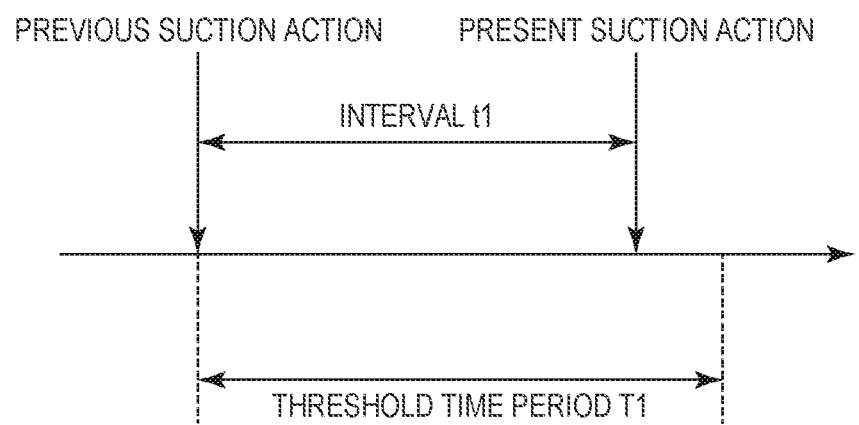
FIG. 2 is a graph showing a first example in which an abnormal state is detected, according to the first embodiment of the present invention.

FIG. 2 is a graph showing a first example in which the control unit 340 detects that the sensor unit 330 is in the abnormal state. In the first example, the control unit 340 detects, based on an interval between the suction actions, that the sensor unit 330 is in the abnormal state.

The control unit 340 acquires an output for detecting the suction action from the sensor unit 330, and acquires the information of time associated with the output from the time measurement unit 341. As shown in FIG. 2, the sensor unit 330 calculates an interval t1 between the previous suction action and the present suction action based on the information of the output and the time. Specifically, the interval t1 is calculated by obtaining a difference between an end time of the previous suction action and a start time of the present suction action.

Then, the control unit 340 determines whether the sensor 330 is in the normal state or the abnormal state based on whether the interval t1 is equal to or less than a threshold time period T1 (for example, 0.1 seconds). When the interval t1 exceeds the threshold time period T1, the control unit 340 determines that the sensor unit 330 is in the normal state. When the interval t1 is equal to or less than the threshold time period T1, the control unit 340 determines that the sensor unit 330 is in the abnormal state.

Figure 3:
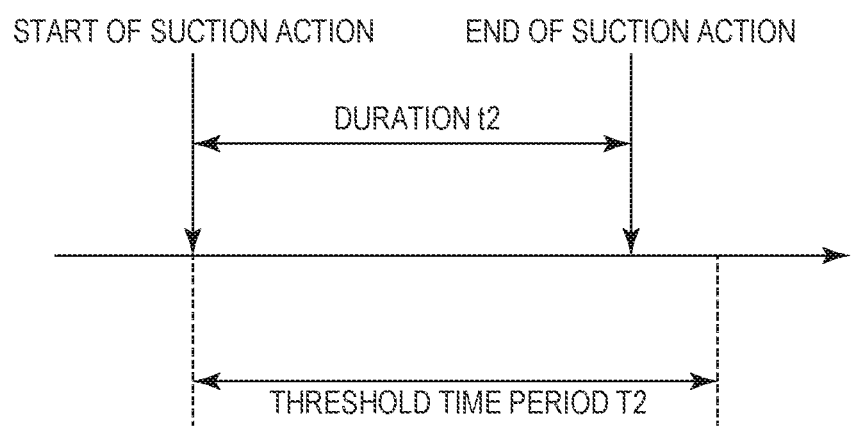
FIG. 3 is a graph showing a second example in which an abnormal state is detected, according to the first embodiment of the present invention.

FIG. 3 is a graph showing a second example in which the control unit 340 detects that the sensor unit 330 is in the abnormal state. In the second example, the control unit 340 detects, based on duration of one suction action, that the sensor unit 330 is in the abnormal state.

The control unit 340 acquires an output for detecting the suction action from the sensor unit 330, and acquires the information of time associated with the output from the time measurement unit 341. As shown in FIG. 3, the sensor unit 330 calculates duration t2 of one suction action defined from a difference between the start time and the end time of the sucking operation, based on the information of the output and the time.

Then, the control unit 340 determines whether the sensor 330 is in the normal state or the abnormal state based on whether the duration t2 of the suction action is equal to or less than a threshold time period T2 (for example, 0.1 seconds). When the duration t2 exceeds the threshold time period T2, the control unit 340 determines that the sensor 330 is in the normal state. When the duration t2 is equal to or less than the threshold time period T2, the control unit 340 determines that the sensor 330 is in the abnormal state.

Figure 4:
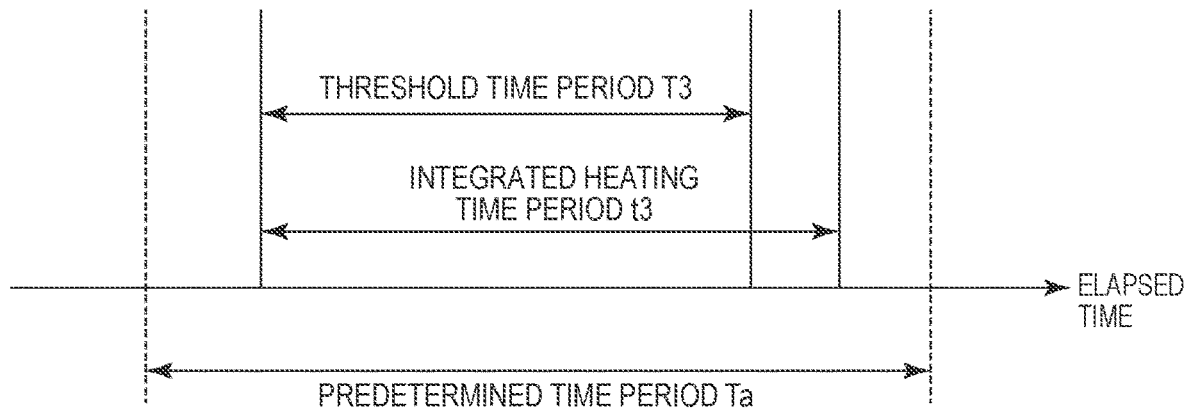
FIG. 4 is a graph showing a third example in which an abnormal state is detected, according to the first embodiment of the present invention.

FIG. 4 is a graph showing a third example in which the control unit 340 detects that the sensor unit 330 is in the abnormal state. In the third example, the control unit 340 detects that the sensor unit 330 is in the abnormal state, based on an integrated heating time period for which the aerosol source is heated by the load 130 within a predetermined time period.

The control unit 340 acquires an output for detecting the suction action from the sensor unit 330, and acquires the information of time associated with the output from the time measurement unit 341. Then, the control unit 340 calculates a total time period for which the sensor unit 330 detects the suction action within a predetermined time period Ta (for example, 30 seconds), that is, an integrated heating time period t3 for which the aerosol source is heated by the load 130 within the predetermined time period Ta, based on the information of the output and the time.

Then, the control unit 340 determines whether the sensor unit 330 is in the normal state or the abnormal state based on whether the integrated heating time period t3 within the predetermined time period Ta is equal to or greater than a threshold time period T3 (for example, 20 seconds). When the integrated heating time period t3 within the predetermined time period Ta is less than the threshold time period T3, the control unit 340 determines that the sensor 330 is in the normal state. When the integrated heating time period t3 within the predetermined time period Ta is equal to or greater than the threshold time period T3, the control unit 340 determines that the sensor 330 is in the abnormal state. Specifically, for example, when the integrated heating time period within 30 seconds exceeds 20 seconds, the control unit 340 determines that the sensor 330 is in the abnormal state.

Figure 5:
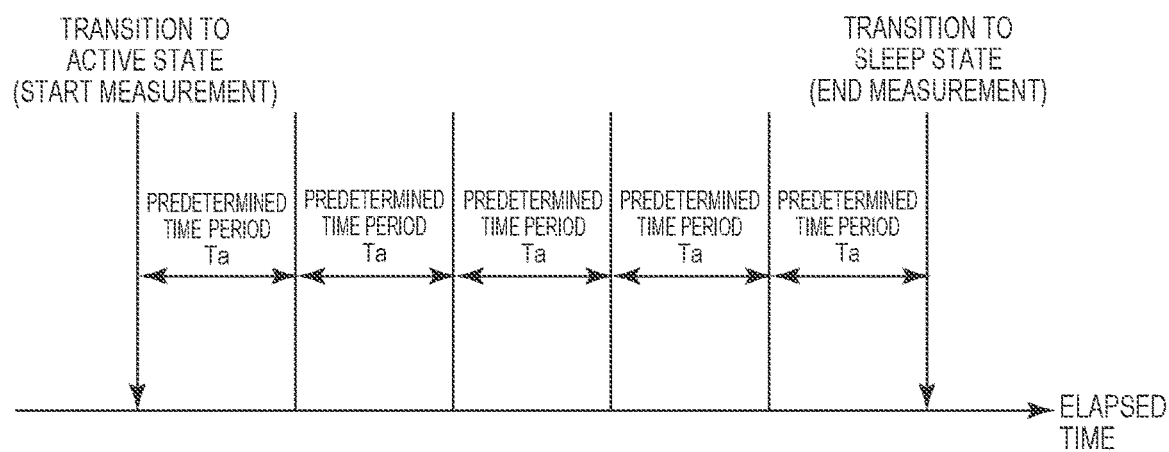
FIG. 5 is a graph showing an example of measurement of a predetermined time period Ta, according to the first embodiment of the present invention.

Note that, for example, as shown in FIG. 5, the above-described predetermined time period Ta may be repeatedly measured starting from when the aerosol generation device 1 undergoes the transition from the sleep state to the normal state by pressing the power supply button 310. Since such a configuration makes it possible to always detect the state of the sensor unit 330 in the normal state in which the user's suction action can be detected, the control unit 340 can detect that the sensor unit 330 has changed to the abnormal state, without fail.

Figure 6:
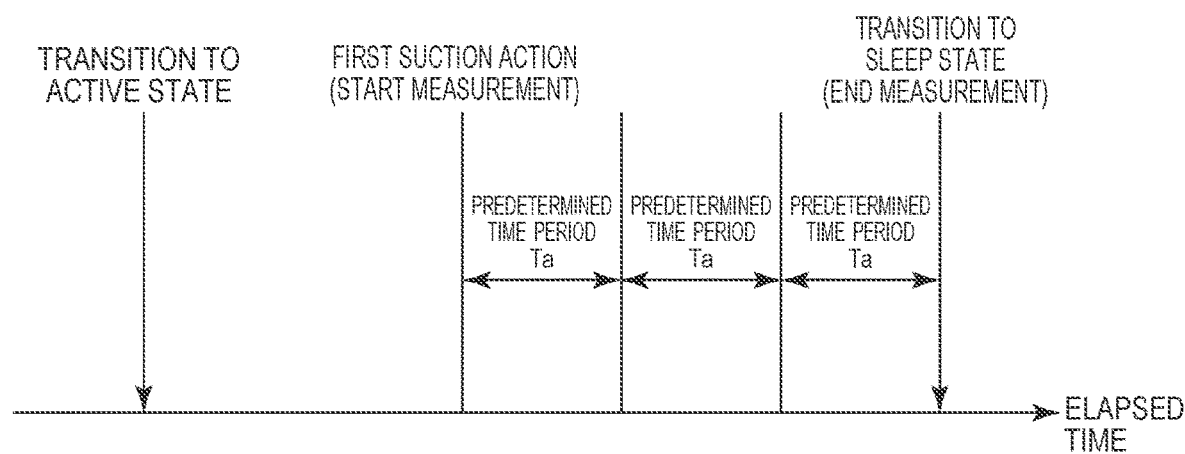
FIG. 6 is a graph showing another example of measurement of a predetermined time period Ta, according to the first embodiment of the present invention.

For example, as shown in FIG. 6, the above-described predetermined time period Ta may be repeatedly measured starting from when the sensor unit 330 detects the suction action for the first time after the aerosol generation device 1 undergoes the transition from the sleep state to the normal state by pressing the power supply button 310. Such a configuration enables the control unit 340 to detect that the sensor unit 330 has changed to the abnormal state, without fail. In addition, since the startup time period of the time measurement unit 341 can be minimized, the energy saving can be achieved.

Figure 7:
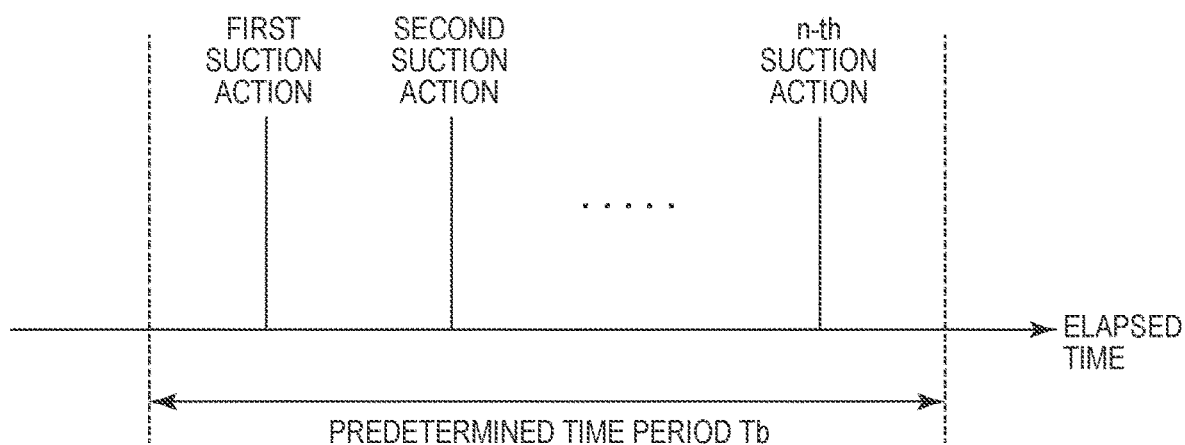
FIG. 7 is a graph showing a fourth example in which an abnormal state is detected, according to the first embodiment of the present invention.

FIG. 7 is a graph showing a fourth example in which the control unit 340 detects that the sensor unit 330 is in the abnormal state. In the fourth example, the control unit 340 detects that the sensor unit 330 is in the abnormal state, based on the number of times that the sensor unit 330 has detected the suction action within a predetermined time period.

The control unit 340 acquires an output for detecting the suction action from the sensor unit 330, and acquires the information of time associated with the output from the time measurement unit 341. Then, the control unit 340 calculates the number of times that the sensor unit 330 has detected the suction action within a predetermined time period Tb (for example, 50 seconds), based on the information of the output and the time.

Then, the control unit 340 determines whether the sensor unit 330 is in the normal state or the abnormal state based on whether the number of times that the sensor unit 330 has detected the suction action within the predetermined time period Tb is equal to or greater than N times (for example, 40 times). When the number of times that the sensor unit 330 has detected the suction action within the predetermined time period Tb is less than N times, the control unit 340 determines that the sensor 330 is in the normal state. When the number of times that the sensor unit 330 has detected the suction action within the predetermined time period Tb is equal to or greater than N times, the control unit 340 determines that the sensor 330 is in the abnormal state. Note that the predetermined time period Tb is repeatedly measured in the same manner as the above-described Ta, for example. Such a configuration enables the control unit 340 to detect that the sensor unit 330 has changed to the abnormal state, without fail. In addition, since the startup time period of the time measurement unit 341 can be minimized, the energy saving can be achieved.

Here, in the first example, the interval between the suction actions is short and the load 130 is maintained in a high temperature state. Therefore, it is assumed that the aerosol source soaked up and held by the supply unit 120 from the storage unit 110 to be supplied to the load 130 is continuously heated. Accordingly, it is assumed that the aerosol source is depleted, that is, the generation of aerosol is gradually decreased.

In the second example, the duration of the suction action is short, and the load 130 cannot be warmed sufficiently. Therefore, it is assumed that the aerosol is not generated by the load 130.

In the third and fourth examples, the aerosol source is excessively heated by the load 130. Therefore, it is assumed that the aerosol source soaked up and held by the supply unit 120 from the storage unit 110 to be supplied to the load 130 is depleted. Accordingly, it is assumed that the generation of aerosol is gradually decreased. Note that when the sensor unit 330 is in the normal state, the aerosol source is not excessively heated by the load 130. Therefore, it is assumed that the aerosol source held by the supply unit 120 is not depleted.

The behavior of the sensor unit 330 shown in each of the first to fourth examples hardly occurs while the aerosol generation device 1 is usually used by the user. That is, in each of the first to fourth examples, the suction action detected by the sensor unit 330 is not a user's suction action but a suction action due to the trouble in the sensor unit 330. In other words, in each of the first to fourth examples, the suction action detected by the sensor unit 330 is a suction action caused and detected by the sensor unit 330 itself that has the trouble. Accordingly, it is determined that the sensor unit 330 that exhibits the above-described behavior shown in each of the first to fourth examples has the trouble.

As described above, it can be said that the output value from the sensor unit 330 that is determined, by the control unit 340, to be in the normal state is different from the output value from the sensor unit 330 that is determined, by the control unit 340, to be in the abnormal state.

Note that after the power supply button 310 is pressed and the aerosol generation device 1 undergoes the transition from the sleep state to the active state, the control unit 340 always performs a process of detecting whether the above-described sensor unit 330 is in the normal state or the abnormal state (hereinafter, referred to as a "state detection process"). On the other hand, when the power supply button 310 is pressed and the power supply unit 300 undergoes the transition from the active state to the sleep state, the control unit 340 does not perform the state detection process. Note that the state detection process will be described in detail later.

The memory unit 350 is, for example, a non-volatile memory. The memory unit 350 stores various types of data and programs for operating the aerosol generation device 1. The memory unit 350 stores a program (or firmware) for executing the state detection process, for example.

In addition, when the control unit 340 detects that the sensor unit 330 is in the abnormal state, the memory unit 350 stores information on such an abnormal state. Specifically, the memory unit 350 stores the content of the trouble that has occurred in the sensor unit 330.

Furthermore, the memory unit 350 stores the number of times that the control unit 340 has detected that the sensor unit 330 is in the abnormal state (hereinafter, referred to as the "number of times of detection") and a limit threshold that is a value limiting the state transition of the aerosol generation device 1 from the sleep state to the active state. The number of times of detection and the limit threshold will be described in detail later.

The notification unit 360 is, for example, a light emitting diode. The notification unit 360 emits light based on the control by the control unit 340. For example, when the control unit 340 detects that the sensor unit 330 is in the abnormal state, the notification unit 360 emits light based on the control by the control unit 340. Examples of the color of light emitted from the notification unit 360 can include, but not particularly limited to, a cold (bluish) color, a warm (reddish) color, and the like.

In addition, the notification unit 360 may be provided, for example, along the circumferential direction of the upstream end of the power supply unit 300 and installed so that the entire end may emit light. Furthermore, for example, the notification unit 360 may be provided along the circumferential direction of the power supply button 310 and installed so that the periphery of the power supply button 310 emits light.

Figure 8:
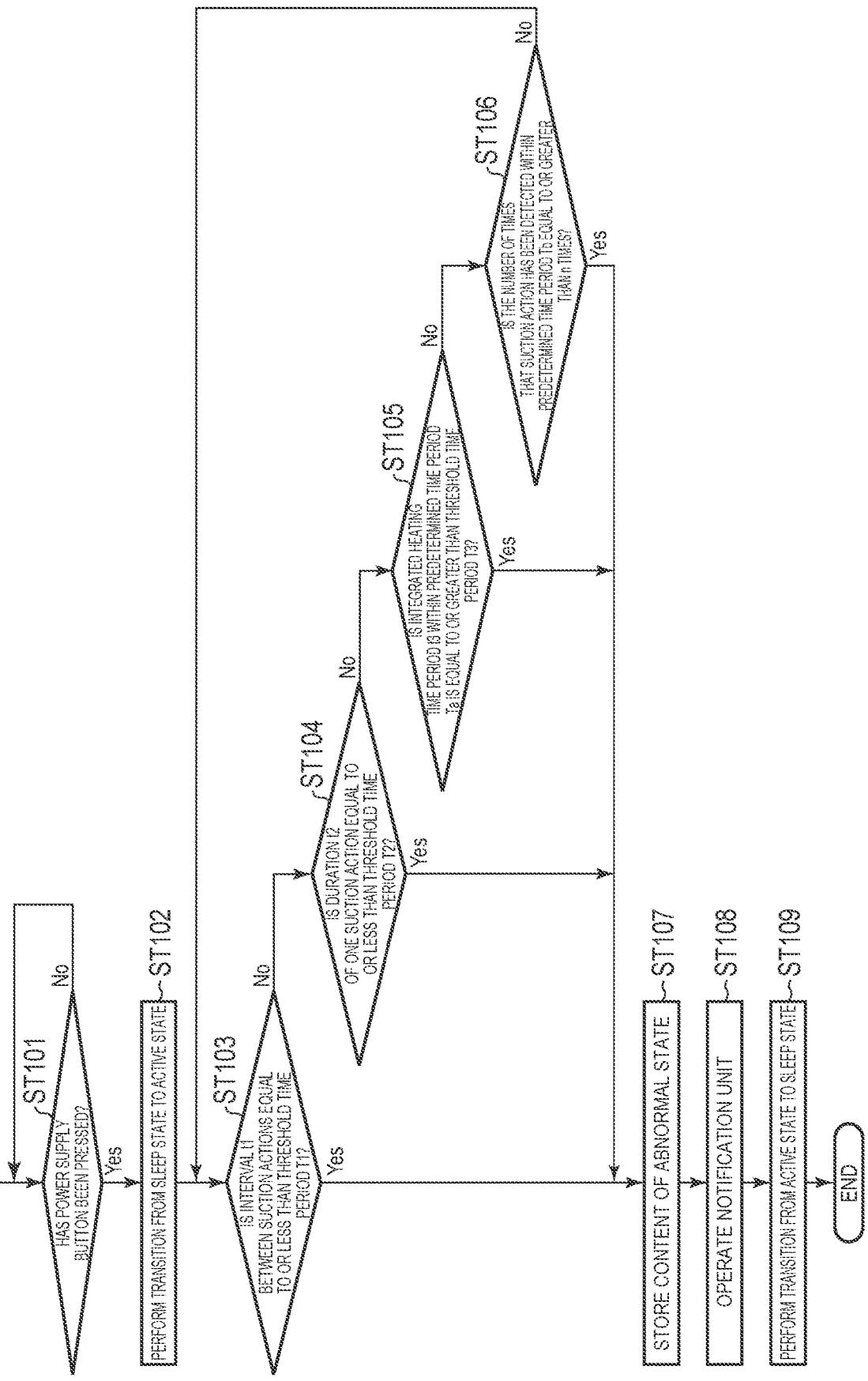
FIG. 8 is a flowchart illustrating an example of a state detection process according to the first embodiment of the present invention.

Next, the state detection process will be described in more detail. FIG. 8 is a flowchart illustrating an example of the state detection process to be performed by the control unit 340.

The control unit 340 determines whether the power supply button 310 has been pressed while the aerosol generation device 1 is in the sleep state (ST101). When the control unit 340 does not determine that the power supply button 310 has been pressed (ST101: NO), the process in step ST101 is performed again. That is, the aerosol suction device 1 is in the sleep state until the power supply button 310 is pressed.

When determining that the power supply button 310 has been pressed (ST101: YES), the control unit 340 causes the aerosol generation device 1 to undergo the transition from the sleep state to the active state (ST102).

Then, the control unit 340, as described above, determines whether the sensor 330 is in the normal state or the abnormal state based on whether the interval t1 between the previous suction action and the present suction action is equal to or less than the threshold time period T1 (ST103).

When the interval t1 exceeds the threshold time period T1 (ST103: NO), the control unit 340, as described above, determines whether the sensor 330 is in the normal state or the abnormal state based on whether the duration t2 of one suction action is equal to or less the threshold time period T2 (ST104).

When the duration t2 of one suction action exceeds the threshold time period T2 (ST104: NO), the control unit 340, as described above, determines whether the sensor unit 330 is in the normal state or the abnormal state based on whether the integrated heating time period t3 within the predetermined time period Ta is equal to or greater than the threshold time period T3 (ST105).

When the integrated heating time period t3 within the predetermined time period Ta is less than the threshold time period T3 (ST105: NO), the control unit 340, as described above, determines whether the sensor unit 330 is in the normal state or the abnormal state based on whether the number of times that the sensor unit 330 has detected the suction action within the predetermined time period Tb is equal to or greater than N times (ST106).

When the number of times that the sensor unit 330 has detected the suction action within the predetermined time period Tb is less than N times (ST106: NO), the processes of ST103 and the subsequent steps are performed again. Accordingly, the process of determining whether the sensor unit 330 is in the abnormal state is always performed while the aerosol generation device 1 is in the active state.

Here, when the interval t1 is equal to or less than the threshold time period T1 (ST103: YES), when the duration t2 of one suction action is equal to or less than the threshold time period T2 (ST104: YES), when the integrated heating time period t3 within the predetermined time period Ta is equal to or greater than the threshold time period T3 (ST105: YES), or the number of times that the sensor unit 330 has detected the suction action within the predetermined time period Tb is equal to or greater than N times (ST106: YES), that is, when it is determined that the sensor unit 330 is in the abnormal state, the control unit 340 causes the memory unit 350 to store information indicating in which of ST103 to ST106 the control unit 340 detects that the sensor 330 is in the abnormal state (ST107). In other words, the control unit 340 causes the memory unit 350 to store the content of the trouble (the content of the abnormal state) that has occurred in the sensor unit 330. The content of the trouble is thus stored in the memory unit 350, thereby making it possible to easily recognize the content of the trouble without having to perform a special inspection when the aerosol generation device 1 is repaired at a later date. Accordingly, the man-hours required for repair can be significantly reduced.

The control unit 340 operates the notification unit 360 (ST108). Specifically, the control unit 340 causes the notification unit 360 to emit light. This makes it possible to notify the user and/or the like who is using the aerosol generation device 1 that the sensor unit 330 has a trouble.

The control unit 340 causes the aerosol generation device 1 to undergo the transition from the active state to the sleep state (ST109). In the case where the trouble has occurred in the sensor unit 330, the aerosol suction device 1 thus undergoes the transition to the sleep state in which the aerosol is not generated, so that the electric power can be prevented from being supplied to each portion of the aerosol generation device 1, even if the aerosol cannot be normally generated. That is, the waste of the electric power can be prevented.

As described above, in the aerosol generation device 1 in the present embodiment, the control unit 340 detects whether the sensor unit 330 is in the normal state or the abnormal state based on an output for detecting the suction action from the sensor unit 330 and the information of time associated with the output from the time measurement unit 341. Specifically, the control unit 340 detects that the sensor unit 330 is in the abnormal state when at least one of the interval between the suction actions calculated based on the information of the output and the time, the duration of one suction action, the integrated heating time period of the load 130 within the predetermined time period, and the number of times of suction action within the predetermined time period satisfies a predetermined condition. Accordingly, the aerosol generation device 1 in the present embodiment can detect the occurrence of a trouble in the sensor.

According to the present embodiment, in the case where a trouble has occurred in the sensor, such a trouble can be detected, thereby making it possible to prevent the aerosol source from being atomized by the aerosol generation device and being wasted, when the user does not perform the suction action, for example. That is, the aerosol generation device in the present embodiment can achieve the effects of resource saving and energy saving.

In the present embodiment, the state detection process to be performed by the control unit 340 has been described by the example illustrated in FIG. 8, but is not limited thereto. For example, the state detection process to be performed by the control unit 340 may be as in the example illustrated in FIG. 9.

Figure 9:
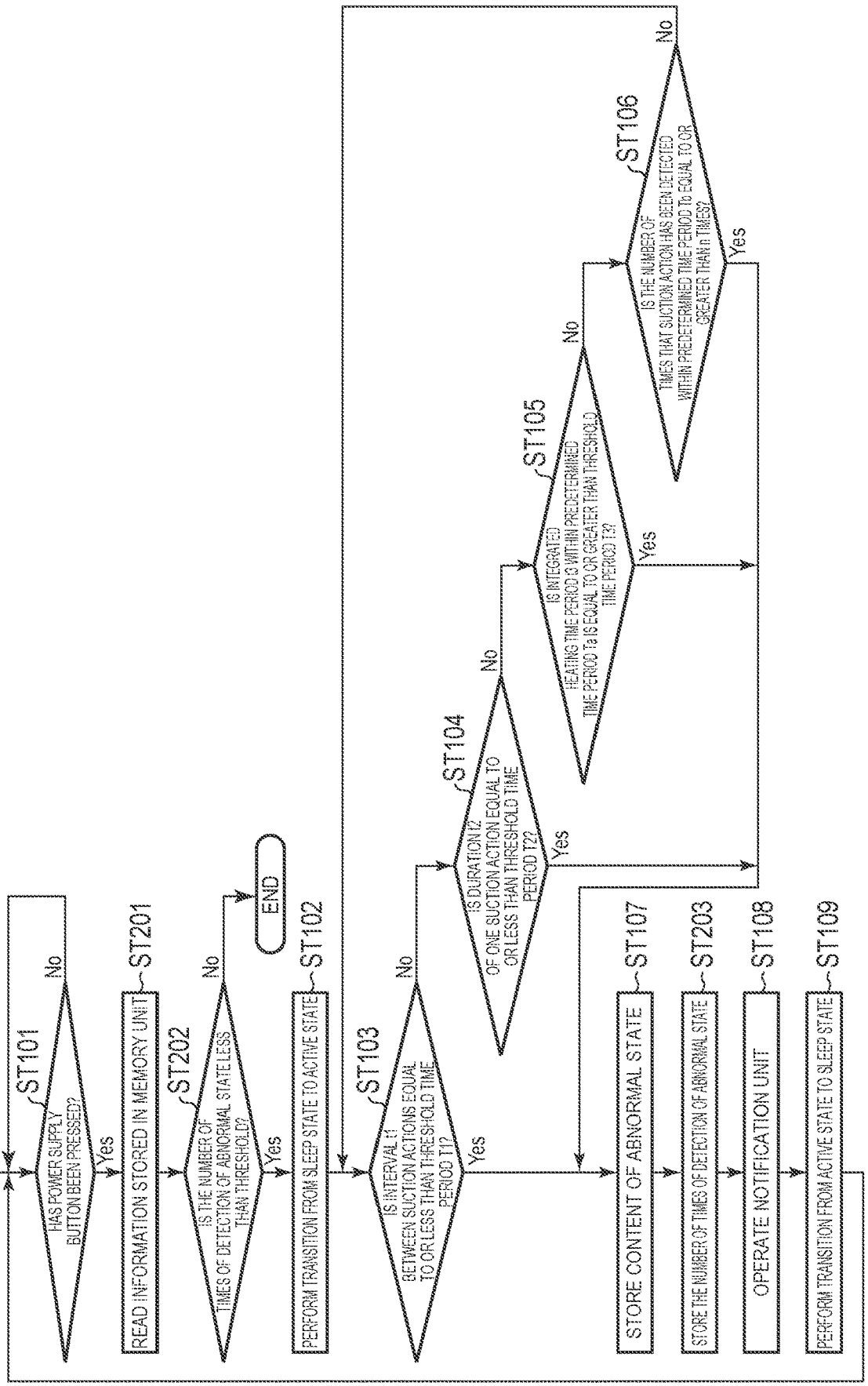
FIG. 9 is a flowchart illustrating another example of a state detection process according to the first embodiment of the present invention.

A flowchart illustrated in FIG. 9 is different from the flowchart illustrated in FIG. 8 in that ST201 to ST203 are added, and the process of ST101 is performed again after the process of ST109. Note that ST203 is a process in which the control unit 340 causes the memory unit 350 to store the number of times that the control unit 340 has detected that the sensor unit 330 is in the abnormal state (the number of times of detection).

Hereafter, the flowchart illustrated in FIG. 9 will be described, mainly focusing on the above-described differences, assuming that the process of ST203 is already performed a plurality of times, that is, the control unit 340 detects, a plurality of times, that the sensor unit 330 is in the abnormal state.

In the flowchart illustrated in FIG. 9, when the control unit 340 detects that the sensor unit 330 is in the abnormal state (YES in any step of ST103, ST104, ST105 and ST106), the process of ST101 is performed again after the processes of ST107, ST203, ST108, and ST109. Accordingly, in the flowchart illustrated in FIG. 9, the process of ST203 may be performed a plurality of times. Therefore, it is assumed that the number of times of detection stored in the memory unit 340 may be updated.

When the power supply button 310 is pressed again in ST 101 (ST101: YES), the control unit 340 reads the information stored in the memory unit 350 (ST201). Specifically, the control unit 340 reads the number of times of detection and the limit threshold which is a threshold limiting the state transition of the aerosol generation device 1 from the sleep state to the active state.

Then, the control unit 340 determines whether the number of times of detection is less than the limit threshold (ST202). When the number of times of detection is less than the limit threshold (ST202: YES), the processes of ST102 and the subsequent steps are performed. For example, when the number of times of detection is 2 and the limit threshold is 3, the processes of ST102 and the subsequent steps are performed.

On the other hand, when the number of times of detection is equal to or greater than the limit threshold (ST202: NO), the process ends. For example, when the number of times of detection is 3 and the limit threshold is 3, the process ends. That is, the aerosol generation device 1 does not undergo the transition from the sleep state to the active state afterwards. The following is the reason why the state transition of the aerosol generation device 1 is controlled based on the comparison between the number of times of detection and the limit threshold.

When being wet with the aerosol source that has leaked out from the storage unit 110, the sensor unit 330 may temporarily malfunction. Specifically, the diaphragm in the sensor unit 330 does not normally vibrate due to being wet with the aerosol source, which may cause the malfunction of the sensor unit 330. Then, the control unit 340 may detect, based on such malfunction, that the sensor unit 330 is in the abnormal state. When the wetting with the aerosol source is eliminated by drying or the like, the diaphragm is often returned to a normal vibration state. That is, the malfunction due to the wetting with the aerosol source can be often eliminated when the wetting is dried.

Based on such a fact, when the number of times of detection is less than the limit threshold, the abnormal state of the sensor unit 330 is considered to be caused by temporary malfunction due to the wetting with the aerosol source. At this time, when the power supply button 310 is pressed, the aerosol generation device 1 is configured to undergo the transition to the active state again.

On the other hand, when the number of times of detection reaches the threshold or more, the abnormal state of the sensor unit 330 is considered to be caused by a permanent trouble. At this time, the aerosol generation device 1 does not undergo the transition from the sleep state to the active state.

Accordingly, in the flowchart of the detection process illustrated in FIG. 9, a determination is made whether the abnormal state of the sensor unit 330 is temporarily caused by the leakage of the aerosol source or is permanently caused by a short circuit or the like, and the state transition of the aerosol generation device 1 is controlled based on such a determination. Accordingly, this can prevent a condition where the aerosol generation device 1 cannot be used even though the aerosol generation device 1 does not have a permanent trouble, whereby the convenience in using the aerosol generation device 1 can be improved.

In the present embodiment, the description has been made assuming that the aerosol generation device 1 generates the aerosol in response to the user's suction action, but the configuration of the aerosol generation device 1 of the present invention is not limited thereto. For example, the aerosol generation device 1 may be configured to generate invisible vapor in response to the user's suction action. Even in such a configuration, the same effects as those of the above-described embodiment can be obtained.

In the present embodiment, the description has been made assuming that the notification unit 360 emits the light according to the control by the control unit 340, but the configuration of the notification unit 360 of the present invention is not limited thereto. For example, the notification unit 360 may be configured to vibrate in a predetermined vibration pattern or output a predetermined sound when the control unit 340 detects that the sensor unit 330 is in the abnormal state. Alternatively, the notification unit 360 may make a notification by combining them. Specifically, for example, the notification unit 360 may make a notification with a combination of light and vibration, or may make a notification with a combination of light, vibration, and sound.

Second Embodiment

Hereinafter, the present embodiment will be described with reference to the drawings. Note that in the following description, approximately or substantially the same functions and constituent elements are denoted by the same reference signs, and are described only when necessary.

In the following description, it is assumed that an aerosol generation device according to the present embodiment is, for example, a heated cigarette or an electronic cigarette. However, the aerosol generation device according to the present embodiment may be an aerosol generation device of another type or usage, such as a medical nebulizer.

Figure 10:
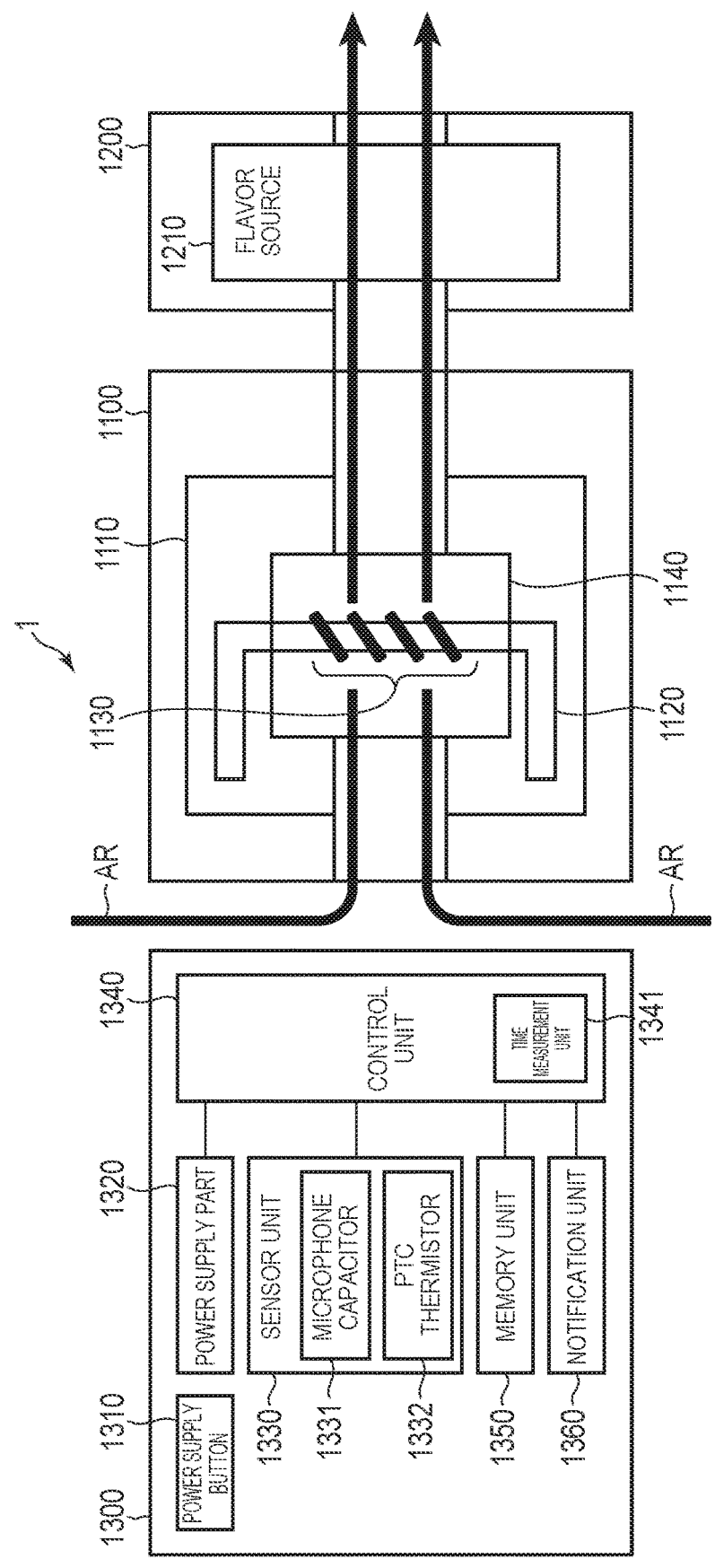
FIG. 10 is a block diagram illustrating an example of a schematic configuration of an aerosol generation device according to a second embodiment of the present invention.

FIG. 10 is a block diagram illustrating an example of a schematic configuration of an aerosol generation device 1000 according to the present embodiment.

As illustrated in FIG. 1, the aerosol generation device 1000 includes a cartridge unit 1100, a capsule unit 1200, and a power supply unit 1300. The aerosol generation device 1000 is configured, for example, in a substantially cylindrical shape, so that a user can easily hold the aerosol generation device 1000. Note that the cartridge unit 1100, the capsule unit 1200, and the power supply unit 1300 may be configured to be connected to one another in a non-detachable or detachable manner.

As illustrated in FIG. 10, the cartridge unit 1100 includes a storage unit 1110, a supply unit 1120, and an atomization unit 1140 provided with a load 1130.

The storage unit 1110 is a container for storing a liquid aerosol source to be atomized through heating. The aerosol source is, for example, a polyol-based material such as glycerin or propylene glycol. The aerosol source may also be a liquid mixture that contains a nicotine liquid, water, a flavoring agent, etc. Alternatively, the aerosol source may also be a solid for which the storage unit 1110 is unnecessary.

The supply unit 1120 is, for example, a wick that is formed by twisting a fiber material such as glass fibers. One end of the supply unit 1120 is connected to the storage unit 1110. The other end of the supply unit 1120 is connected to the load 1130 or is arranged in the vicinity of the load 1130. With such an arrangement, the supply unit 1120 can soak up the aerosol source from the storage unit 1110 and guide the aerosol source to the load 1130 or the vicinity of the load 1130. Note that the wick made of porous ceramic may also be used for the supply unit 1120.

The load 1130 provided in the atomization unit 1140 is a coil-shaped heater, for example, and generates heat when the electric power is supplied thereto. The load 1130 may be wound around the supply unit 1120 or may be covered by the supply unit 1120. The electric power is supplied to the load 1130 from a power supply part 1320, which will be described later, based on the control by a control unit 1340, which will be described later, included in the power supply unit 1300. When the electric power is supplied to the load 1130, the aerosol source guided by the supply unit 1120 is heated by the load 1130, whereby aerosol is generated.

The capsule unit 1200 includes a flavor source 1210, as illustrated in FIG. 10.

The flavor source 1210 includes a raw material piece of a plant material that imparts a flavor component to the aerosol. For example, shredded tobacco or a forming body obtained by forming a tobacco material such as a tobacco raw material in a granular form or a sheet form is used as the raw material piece which is a component of the flavor source. In addition, a plant (for example, mint, a herb, or the like) other than tobacco may be used as the raw material piece which is a component of the flavor source 1210. The flavor source 1210 may be provided with a flavor such as menthol.

Each arrow in FIG. 10 indicates the flow of air in the cartridge unit 1100 and the capsule unit 1200. The air taken in from the outside through an air intake opening (not illustrated) is mixed with the aerosol in the process of passing through the aerosol generation device 1000 (the cartridge unit 1100 and the capsule unit 1200) to which a flavor component is added, and the resultant mixture is sucked by the user. Specifically, the air taken in from the outside passes through the atomization unit 1140 in the cartridge unit 1100. While passing through the atomization unit 1140, the air is mixed with the aerosol generated by the load 1130 provided in the atomization unit 1140. Then, when the air mixed with the aerosol passes through the capsule unit 1200, the flavor component derived from the flavor source 1210 included in the capsule unit 1200 is added to the air mixed with the aerosol. Then, the air mixed with the aerosol and added with the flavor component is sucked by the user from the end portion of the capsule unit 1200. That is, the aerosol to which the flavor component is added is sucked by the user.

As illustrated in FIG. 10, the power supply unit 1300 includes a power supply button 1310, the power supply part 1320, a sensor unit 1330, the control unit 1340, a memory unit 1350, and a notification unit 1360. Note that the sensor unit 1330 includes a microphone capacitor 1331 which is a first sensor, and a PTC thermistor 1332 which is a second sensor. In addition, the control unit 1340 includes a time measurement unit 1341.

The power supply button 1310 is a button for causing an operating state transition of the aerosol generation device 1000. When the power supply button 1310 is pressed to turn on the power supply, the aerosol generation device 1000 undergoes the transition to an active state. When the power supply button 1310 is pressed to turn off the power supply while the aerosol generation device 1000 is in the active state, the aerosol generation device 1000 undergoes the transition from the active state to a sleep state.

The power supply part 1320 is, for example, a rechargeable battery such as a lithium-ion secondary battery, and its type is not limited. The power supply part 1320 supplies the electric power to each portion of the aerosol generation device 1000 based on the control by the control unit 1340.

The sensor unit 1330 has at least a function of detecting a user's suction action (an action for requesting the aerosol generation device 1000 to generate the aerosol) and a function of detecting troubles of the detection function and the like. As illustrated in FIG. 10, the sensor unit 1330 includes a microphone capacitor 1331 which is a first sensor, and a PTC thermistor 1332 which is a second sensor.

The microphone capacitor 1331 detects the user's suction action.

The PTC thermistor 1332 has a function of preventing an excessive current from flowing in each element that constitutes the sensor unit 1330 (hereinafter, referred to as an "overcurrent protection function") before the excessive current flows therein.

Note that the sensor unit 1330 will be described in detail later.

The control unit 1340 causes the aerosol generation device 1000 to undergo the transition to one of two operating states when the power supply button 1310 is pressed. The two operating states include an active state in which the electric power can be supplied from the power supply part 1320 to each portion of the aerosol generation device 1000 and a sleep state in which no electric power can be supplied from the power supply part 1320 to each portion of the aerosol generation device 1000 or only minimal electric power can be supplied from the power supply part 1320 to each portion of the aerosol generation device 1000. When the sensor unit 1330 detects the user's suction action while the aerosol generation device 1000 is in the active state, the control unit 1340 causes the power supply part 1320 to supply the electric power to the load 1130 to atomize the aerosol source. When the aerosol generation device 1000 is in the sleep state, the control unit 1340 does not cause the power supply part 1320 to supply the electric power to the load 1130 even when the user performs a suction action. Therefore, the aerosol source is not atomized.

The control unit 1340 performs a process of detecting whether the microphone capacitor 1331 is in the normal state or the abnormal state (hereinafter, referred to as a "state detection process"). The state detection process includes a first state detection process of detecting the state of the microphone capacitor 1331 based on the voltage value applied to the PTC thermistor 1332 and a second state detection process of detecting the state of the microphone capacitor 1331 based on the output for detecting the suction action from the microphone capacitor 1331. The first state detection process and the second state detection process will be described in detail later.

Here, the normal state refers to a state in which the microphone capacitor 1331 has no trouble and can normally detect the user's suction action. In other words, the normal state refers to a state in which when the user performs the suction action, the microphone capacitor 1331 detects such a suction action, and the electric power is supplied to the load 1130, whereby the aerosol is generated. Note that the supply of the electric power from the power supply part 1320 to the load 1130 under the control by the control unit 1340 is continuously performed while the microphone capacitor 1331 detects the user's suction action.

The abnormal state refers to a state in which the microphone capacitor 1331 has a trouble, and cannot normally detect the user's suction action. In other words, the abnormal state refers to a state in which even when the user performs the suction action while the aerosol generation device 1000 is in the active state, the microphone capacitor 1331 does not detect such a suction action, and therefore no aerosol is generated. In addition, the abnormal state refers to a state in which the microphone capacitor 1331 falsely detects the user's suction action even though the user does not perform the suction action, and the electric power is supplied to the load 1130, whereby the aerosol is generated.

The control unit 1340 includes the time measurement unit 1341. The time measurement unit 1341 is a meter that can measure the time, such as a clock, or a stopwatch, for example, and its type is not limited. The time measurement unit 1341 measures the time when the control unit 1340 detects the state of the microphone capacitor 1331, as described later. Note that in the present embodiment, the description will be made on an example in which the time measurement unit 1341 is included in the control unit 1340, but the time measurement unit 1341 may be provided outside the control unit 1340.

The memory unit 1350 is, for example, a non-volatile memory. The memory unit 1350 stores various types of data and programs for operating the aerosol generation device 1000. The memory unit 1350 stores a program (or firmware) for executing the state detection process, for example.

The notification unit 1360 is, for example, a light emitting diode. The notification unit 1360 emits light based on the control by the control unit 1340. For example, when the control unit 1340 detects that the sensor unit 1330 is in the abnormal state, the notification unit 1360 emits light based on the control by the control unit 1340. Examples of the color of light emitted from the notification unit 1360 can include, but not particularly limited to, a cold (bluish) color, a warm (reddish) color, and the like.

In addition, the notification unit 1360 may be provided, for example, along the circumferential direction of the upstream end of the power supply unit 1300 and installed so that the entire end may emit light. Furthermore, for example, the notification unit 1360 may be provided along the circumferential direction of the power supply button 1310 and installed so that the periphery of the power supply button 1310 emits light. [0154] (Detailed Description of First State Detection Process) Next, the description will be made on the detail of the sensor unit 1330 and the detail of the first state detection process of detecting the state of the microphone capacitor 1331 based on the voltage value applied to the PTC thermistor 1332.

Figure 11:
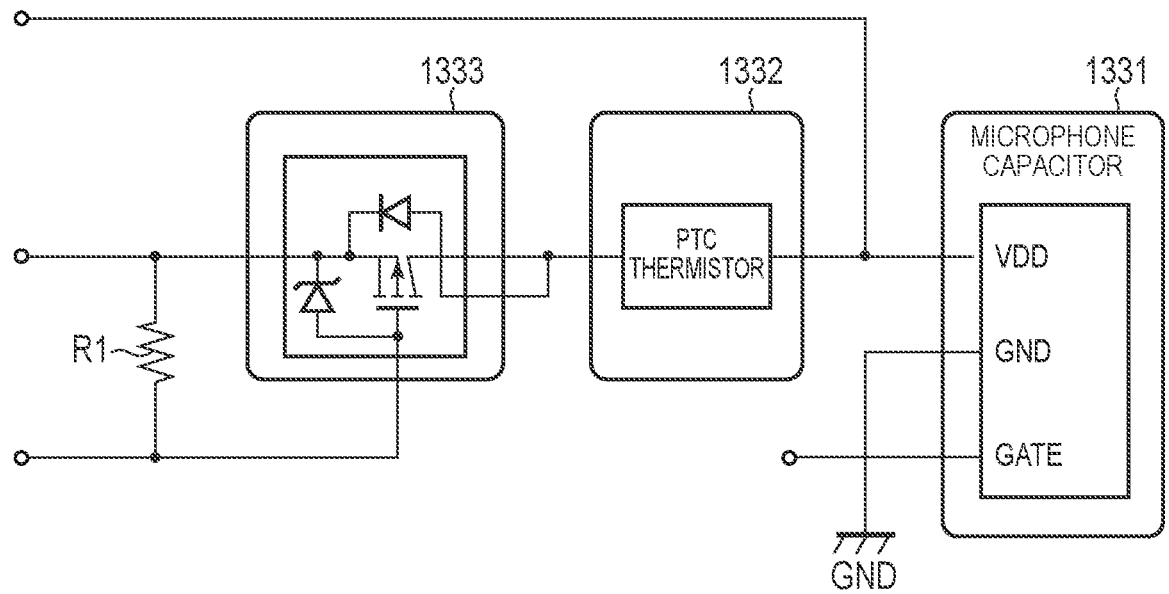
FIG. 11 is a diagram illustrating an example of a circuit configuration of a sensor unit according to the second embodiment of the present invention.

FIG. 11 is a diagram illustrating an example of a circuit configuration of the sensor unit 1330. As illustrated in FIG. 11, the circuit includes the microphone capacitor 1331, the PTC thermistor 1332, and a P-type MOSFET 1333. When the power supply button 1310 is pressed and the aerosol generation device 1000 undergoes the transition from the sleep state to the active state, the base voltage is applied and the drain current flows in the P-type MOSFET 1333. Then, the current flows through the PTC thermistor 1332 and the microphone capacitor 1331, and the PTC thermistor 1332 and the microphone capacitor 1331 are brought into a state in which they can perform the respective functions.

Figure 12:
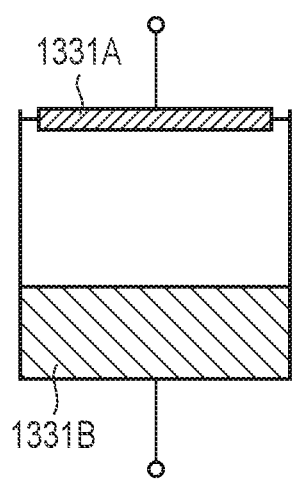
FIG. 12 is a diagram illustrating an example of a configuration of a microphone capacitor according to the second embodiment of the present invention.

FIG. 12 is a diagram illustrating an example of a configuration of the microphone capacitor 1331.

The microphone capacitor 1331 includes a diaphragm 1331A that is a metal plate made to vibrate by changes in sound and pressure due to the user's suction action, and a back plate 1331B that is a fixed metal plate. Since the diaphragm 1331A does not vibrate when there are no changes in sound and pressure due to the user's suction action, the electrostatic capacitance defined by the diaphragm 1331A and the back plate 1331B does not change. On the other hand, when there are changes in sound and pressure due to the user's suction action, the diaphragm 1331A vibrates based on the changes in sound and pressure, and the electrostatic capacitance defined by the diaphragm 1331A and the back plate 1331B changes. The user's suction action is detected based on the change in the electrostatic capacitance.

Figure 13:
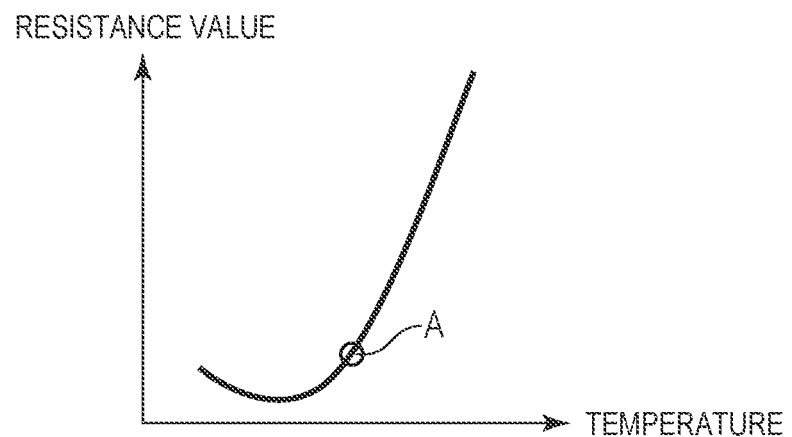
FIG. 13 is a graph showing an example of a resistance-temperature characteristic of a PTC thermistor, according to the second embodiment of the present invention.
Figure 14:
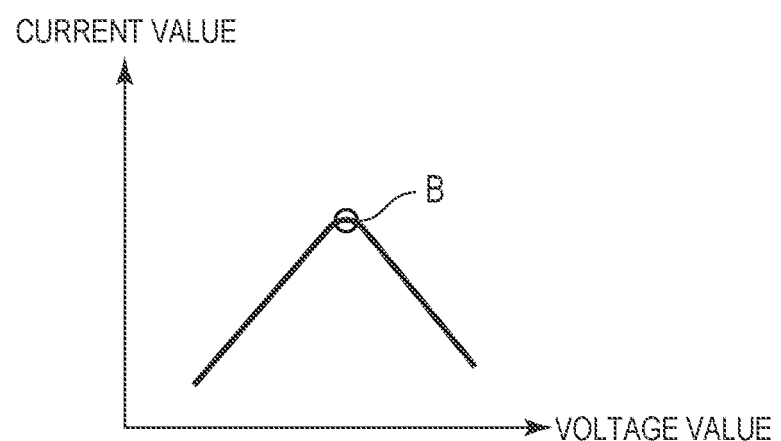
FIG. 14 is a graph showing an example of a voltage-current characteristic of the PTC thermistor, according to the second embodiment of the present invention.

FIGS. 13 and 14 each are a graph showing a characteristic of the PTC thermistor 1332.

FIG. 13 shows an example of a resistance-temperature characteristic of the PTC thermistor 1332, where the vertical axis represents a resistance value and the horizontal axis represents a temperature. As shown in FIG. 13, the resistance value of the PTC thermistor 1332 is a substantially constant value when the temperature of the PTC thermistor 1332 is low (for example, about room temperature), but increases sharply when exceeding a certain temperature value (hereinafter, referred to as a "point A"). Therefore, when the temperature of the PTC thermistor 1332 becomes equal to or higher than the temperature at the point A, the PTC thermistor 1332 functions to increase the resistance value and prevent the excessive current from flowing. That is, the PTC thermistor 1332 performs the overcurrent protection function.

FIG. 14 shows an example of a voltage-current characteristic of the PTC thermistor 1332, where the vertical axis represents a current value and the horizontal axis represents a voltage value. As shown in FIG. 14, in the PTC thermistor 1332, the current value also increases proportionally up to a certain voltage value according to Ohm's law, but since the resistance value increases suddenly when the voltage value exceeds a certain voltage value (hereinafter, referred to as a "point B"), the current value decreases. In other words, when the voltage vale applied to the PTC thermistor 1332 reaches a value exceeding the point B, the PTC thermistor 1332 functions to prevent an excessive current from flowing by increasing the resistance value. That is, the PTC thermistor 1332 performs the overcurrent protection function.

As illustrated in FIG. 12, since the PTC thermistor 1332 is electrically connected to the microphone capacitor 1331, the voltage value applied to the PTC thermistor 1332 is affected by the electrical change in the microphone capacitor 1331. Therefore, the fact that the voltage value of the PTC thermistor 1332 reaches a value exceeding the point B means that the microphone capacitor 1331 has a trouble in that the excessive current tries to flow. Such a trouble is in that a short circuit has occurred in the microphone capacitor 1331, for example. In addition, the electrical change in the microphone capacitor 1331 affects a change in voltage value applied to the microphone capacitor 1331, a change in the current value flowing in the microphone capacitor 1331, and the like.

In the present embodiment, the control unit 1340 performs the first state detection process in view of such characteristics of the sensor unit 1330. Specifically, the control unit 1340 acquires the voltage value applied to the PTC thermistor 1332 based on an output from the PTC thermistor 1332, for example. Then, the control unit 1340 compares the voltage value with a preset voltage threshold equal to or higher than the point B, and detects whether the microphone capacitor 1331 is in the normal state or the abnormal state. Specifically, when the voltage value applied to the PTC thermistor 1332 is equal to or higher than the above-described voltage threshold, the control unit 1340 detects that the microphone capacitor 1331 is in the abnormal state. That is, the control unit 1340 detects that the microphone capacitor 1332 has the trouble (a short circuit).

(Detailed Description of Second State Detection Process)

Next, the description will be made on the detail of the second state detection process of detecting the state of the microphone capacitor 1331 based on the output for detecting the user's suction action that is output from the sensor unit 1330 (more specifically, the microphone capacitor 1331 included in the sensor unit 1330). The following four examples are examples in which it is detected, in the second state detection process that the microphone capacitor 1331 is in the abnormal state.

Figure 15:
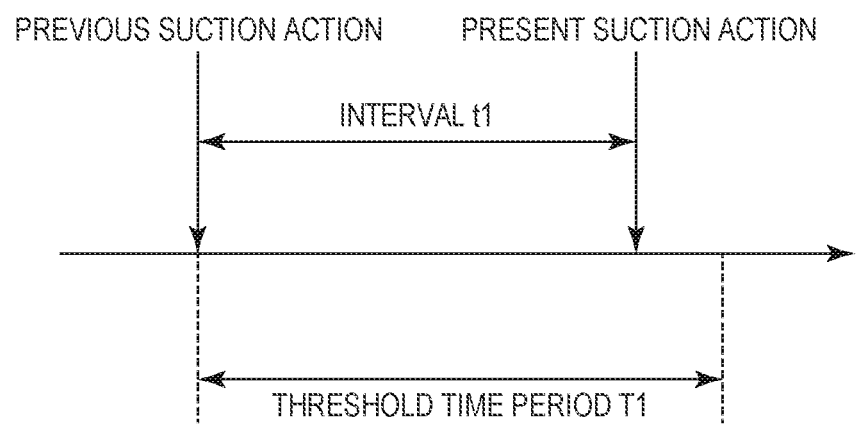
FIG. 15 is a graph showing a first example in which an abnormal state is detected, according to the second embodiment of the present invention.

FIG. 15 is a graph showing a first example in which the control unit 1340 detects, in the second state detection process, that the microphone capacitor 1331 is in the abnormal state. In the first example, the control unit 1340 detects, based on an interval between the suction actions, that the microphone capacitor 1331 is in the abnormal state.

The control unit 1340 acquires an output for detecting the suction action from the microphone capacitor 1331, and acquires the information of time associated with the output from the time measurement unit 1341. As shown in FIG. 15, the microphone capacitor 1331 calculates an interval t1 between the previous suction action and the present suction action, based on the information of the output and the time. Specifically, the interval t1 is calculated by obtaining a difference between an end time of the previous suction action and a start time of the present suction action.

Then, the control unit 1340 determines whether the microphone capacitor 1331 is in the normal state or the abnormal state based on whether the interval t1 is equal to or less than a threshold time period T1 (for example, 0.1 seconds). When the interval t1 exceeds the threshold time period T1, the control unit 1340 determines that the microphone capacitor 1331 is in the normal state. When the interval t1 is equal to or less than the threshold time period T1, the control unit 1340 determines that the microphone capacitor 1331 is in the abnormal state.

Figure 16:
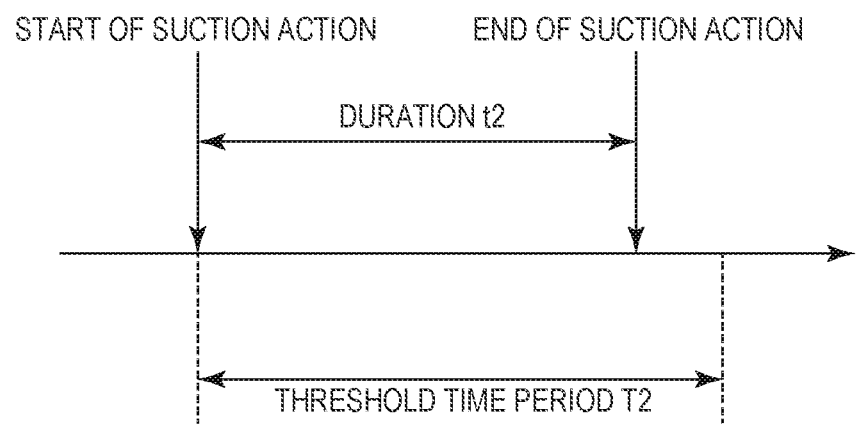
FIG. 16 is a graph showing a second example in which an abnormal state is detected, according to the second embodiment of the present invention.

FIG. 16 is a graph showing a second example in which the control unit 1340 detects, in the second state detection process, that the microphone capacitor 1331 is in the abnormal state. In the second example, the control unit 1340 detects, based on duration of one suction action, that the microphone capacitor 1331 is in the abnormal state.

The control unit 1340 acquires an output for detecting the suction action from the microphone capacitor 1331 (or the sensor unit 1330; the same applies to the following description), and acquires the information of time associated with the output from the time measurement unit 1341. As shown in FIG. 16, the microphone capacitor 1331 calculates duration t2 of one suction action defined from a difference between the start time and the end time of the sucking operation, based on the information of the output and the time.

The control unit 1340 determines whether the microphone capacitor 1331 is in the normal state or the abnormal state based on whether the duration t2 of the suction action is equal to or less than a threshold time period T2 (for example, 0.1 seconds). When the duration t2 exceeds the threshold time period T2, the control unit 1340 determines that the microphone capacitor 1331 is in the normal state. When the duration t2 is equal to or less than the threshold time period T2, the control unit 1340 determines that the microphone capacitor 1331 is in the abnormal state.

Figure 17:
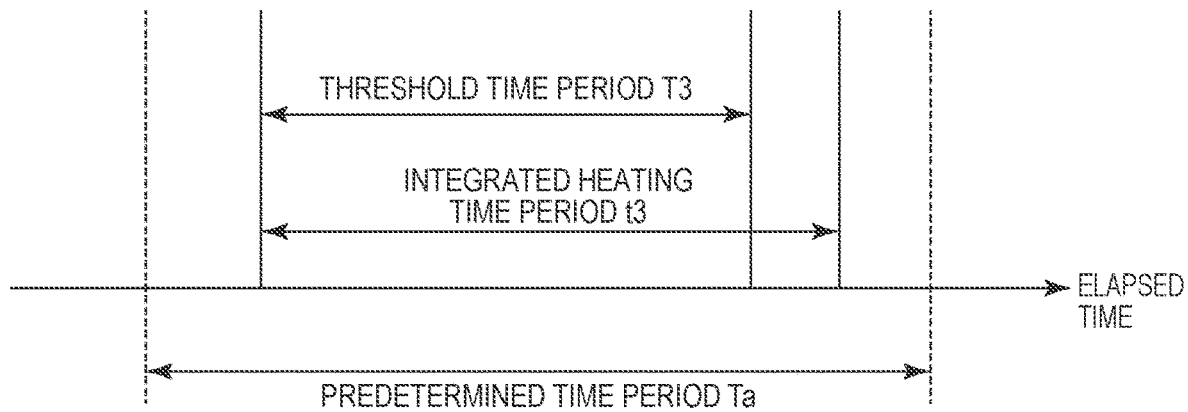
FIG. 17 is a graph showing a third example in which an abnormal state is detected, according to the second embodiment of the present invention.

FIG. 17 is a graph showing a third example in which the control unit 1340 detects, in the second state detection process, that the microphone capacitor 1331 is in the abnormal state. In the third example, the control unit 1340 detects that the microphone capacitor 1331 is in the abnormal state, based on an integrated heating time period for which the aerosol source is heated by the load 1130 within a predetermined time period.

The control unit 1340 acquires an output for detecting the suction action from the microphone capacitor 1331, and acquires the information of time associated with the output from the time measurement unit 1341. Then, the control unit 1340 calculates a total time period for which the microphone capacitor 1331 detects the suction action within a predetermined time period Ta (for example, 30 seconds), that is, an integrated heating time period t3 for which the aerosol source is heated by the load 130 within the predetermined time period Ta, based on the information of the output and the time.

Then, the control unit 1340 determines whether the microphone capacitor 1331 is in the normal state or the abnormal state based on whether the integrated heating time period t3 within the predetermined time period Ta is equal to or greater than a threshold time period T3 (for example, 20 seconds). When the integrated heating time period t3 within the predetermined time period Ta is less than the threshold time period T3, the control unit 1340 determines that the microphone capacitor 1331 is in the normal state. When the integrated heating time period t3 within the predetermined time period Ta is equal to or greater than the threshold time period T3, the control unit 1340 determines that the microphone capacitor 1331 is in the abnormal state. Specifically, for example, when the integrated heating time period within 30 seconds exceeds 20 seconds, the control unit 1340 determines that the microphone capacitor 1331 is in the abnormal state.

Figure 18:
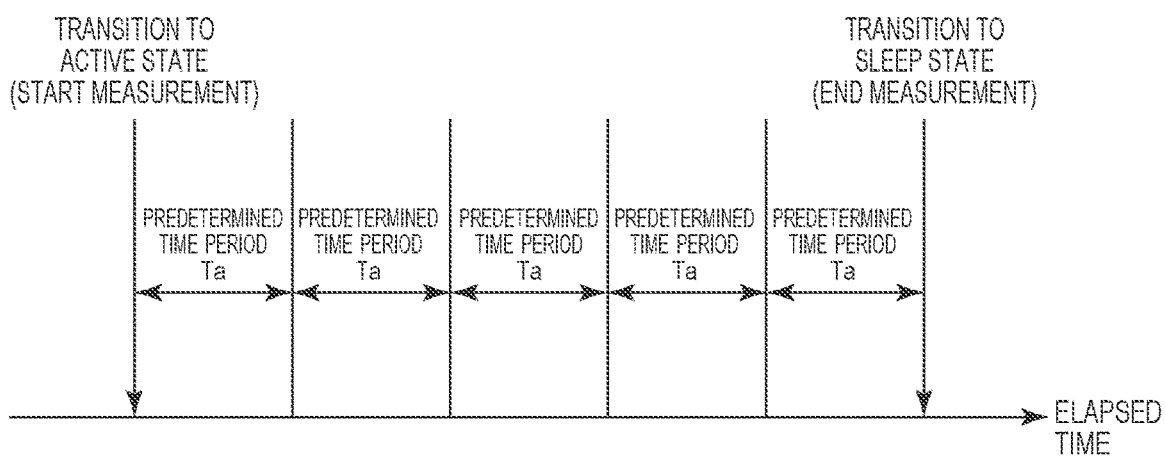
FIG. 18 is a graph showing an example of measurement of a predetermined time period Ta, according to the second embodiment of the present invention.

Note that, for example, as shown in FIG. 18, the above-described predetermined time period Ta may be repeatedly measured starting from when the aerosol generation device 1000 undergoes the transition from the sleep state to the normal state by pressing the power supply button 1310. Since such a configuration makes it possible to always detect the state of the microphone capacitor 1331 in the normal state in which the user's suction action can be detected, the control unit 1340 can detect that the microphone capacitor 1331 has changed to the abnormal state, without fail.

Figure 19:
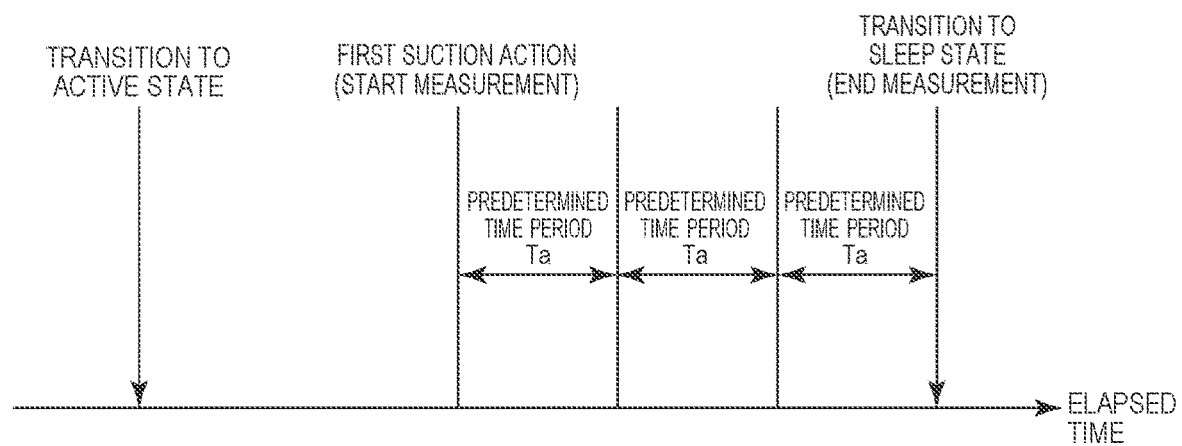
FIG. 19 is a graph showing another example of measurement of a predetermined time period Ta, according to the second embodiment of the present invention.

For example, as shown in FIG. 19, the above-described predetermined time period Ta may be repeatedly measured starting from when the microphone capacitor 1331 detects the suction action for the first time after the aerosol generation device 1000 undergoes the transition from the sleep state to the normal state by pressing the power supply button 1310. Such a configuration enables the control unit 1340 to detect that the microphone capacitor 1331 has changed to the abnormal state, without fail. In addition, since the startup time period of the time measurement unit 1341 can be minimized, the energy saving can be achieved.

Figure 20:
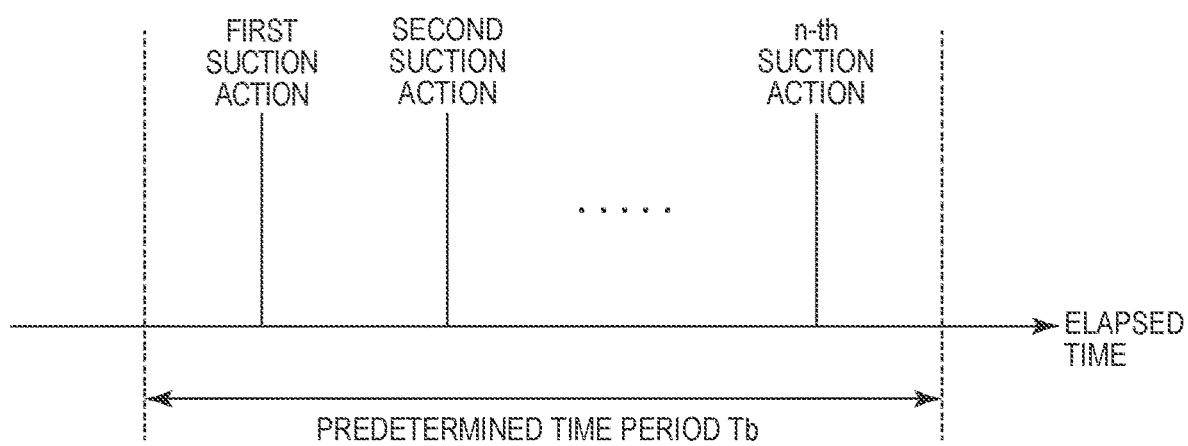
FIG. 20 is a graph showing a fourth example in which an abnormal state is detected, according to the second embodiment of the present invention.

FIG. 20 is a graph showing a fourth example in which the control unit 1340 detects, in the second state detection process, that the microphone capacitor 1331 is in the abnormal state. In the fourth example, the control unit 1340 detects that the microphone capacitor 1331 is in the abnormal state, based on the number of times that the microphone capacitor 1331 has detected the suction action within a predetermined time period.

The control unit 1340 acquires an output for detecting the suction action from the microphone capacitor 1331, and acquires the information of time associated with the output from the time measurement unit 1341. Then, the control unit 1340 calculates the number of times that the microphone capacitor 1331 has detected the suction action within a predetermined time period Tb (for example, 50 seconds), based on the information of the output and the time.

Then, the control unit 1340 determines whether the microphone capacitor 1331 is in the normal state or the abnormal state based on whether the number of times that the microphone capacitor 1331 has detected the suction action within the predetermined time period Tb is equal to or greater than N times (for example, 30 times). When the number of times that the microphone capacitor 1331 has detected the suction action within the predetermined time period Tb is less than N times, the control unit 340 determines that the microphone capacitor 1331 is in the normal state. When the number of times that the microphone capacitor 1331 has detected the suction action within the predetermined time period Tb is equal to or greater than N times, the control unit 340 determines that the microphone capacitor 1331 is in the abnormal state. Note that the predetermined time period Tb is repeatedly measured in the same manner as the above-described Ta, for example. Such a configuration enables the control unit 1340 to detect that the microphone capacitor 1331 has changed to the abnormal state, without fail. In addition, since the startup time period of the time measurement unit 1341 can be minimized, the energy saving can be achieved.

Here, in the first example, the interval between the suction actions is short and the load 1130 is maintained in a high temperature state. Therefore, it is assumed that the aerosol source soaked up and held by the supply unit 1120 from the storage unit 1110 to be supplied to the load 1130 is continuously heated. Accordingly, it is assumed that the aerosol source is depleted, that is, the generation of aerosol is gradually decreased.

In the second example, the duration of the suction action is short, and the load 1130 cannot be warmed sufficiently. Therefore, it is assumed that the aerosol is not generated by the load 1130.

In the third and fourth examples, the aerosol source is excessively heated by the load 1130. Therefore, it is assumed that the aerosol source soaked up and held by the supply unit 1120 from the storage unit 1110 to be supplied to the load 1130 is depleted. Accordingly, it is assumed that the generation of aerosol is gradually decreased. Note that when the sensor unit 1330 is in the normal state, the aerosol source is not excessively heated by the load 1130. Therefore, it is assumed that the aerosol source held by the supply unit 1120 is not depleted.

The behavior of the sensor unit 1330 shown in each of the first to fourth examples hardly occurs while the aerosol generation device 1000 is usually used by the user. That is, in each of the first to fourth examples, the suction action detected by the sensor unit 1330 is not a user's suction action but a suction action due to the trouble in the sensor unit 1330. In other words, in each of the first to fourth examples, the suction action detected by the sensor unit 1330 is a suction action caused and detected by the sensor unit 1330 itself that has the trouble. Accordingly, it is determined that the sensor unit 1330 that exhibits the above-described behavior shown in each of the first to fourth examples has the trouble.

As described above, it can be said that the output value from the sensor unit 1330 that is determined, by the control unit 1340, to be in the normal state is different from the output value from the sensor unit 1330 that is determined, by the control unit 1340, to be in the abnormal state.

(Detailed Description of Memory Portion 1350 and Notification Portion 1360)

Next, the memory unit 1350 and the notification unit 1360 will be described in detail. FIG. 21 is a table showing an example of control information stored in the memory unit 1350. The control information is used when the control unit 1340 controls the notification unit 1360. As shown in FIG. 21, the control information includes a control content for the notification unit 1360 controlled by the control unit 1340 that is associated with each content or cause of a trouble, detected by the control unit 1340, in that the microphone capacitor 1331 is in the abnormal state.

Specifically, for example, when detecting, based on the first state detection process, that the voltage value applied to the PTC thermistor 1332 is equal to or higher than the threshold voltage, the control unit 1340 refers to the control information stored in the memory unit 1350 and generates an error signal corresponding to the detected content. Then, the control unit 1340 causes the notification unit 1350 to emit light four times alternately in a warm color and a cold color, based on the generated error signal.

In addition, for example, when detecting, based on the second state detection process, that the interval t1 between the suction actions is equal to or less the threshold time period T1, the control unit 1340 refers to the control information stored in the memory unit 1350 and generates an error signal corresponding to the detected content. Then, the control unit 1340 causes the notification unit 1350 to emit light six times alternately in a warm color and a cold color, based on the generated error signal.

In addition, for example, when detecting, based on the second state detection process, that the duration t2 of one suction action is equal to or less the threshold time period T2, the control unit 1340 refers to the control information stored in the memory unit 1350 and generates an error signal corresponding to the detected content. Then, the control unit 1340 causes the notification unit 1350 to emit light eight times alternately in a warm color and a cold color, based on the generated error signal.

In addition, for example, when detecting, based on the second state detection process, that the integrated heating time period t3 within the predetermined time period Ta is equal to or greater the threshold time period T3, the control unit 1340 refers to the control information stored in the memory unit 1350 and generates an error signal corresponding to the detected content. Then, the control unit 1340 causes the notification unit 1350 to emit light 10 times alternately in a warm color and a cold color, based on the generated error signal.

In addition, for example, when detecting, based on the second state detection process, that the number of times that the suction action has been detected within the predetermined time period Tb, the control unit 1340 refers to the control information stored in the memory unit 1350 and generates an error signal corresponding to the detected content. Then, the control unit 1340 causes the notification unit 1350 to emit light 12 times alternately in a warm color and a cold color, based on the generated error signal.

As described above, when detecting that the microphone capacitor 1331 is in the abnormal state, the control unit 1340 causes the notification unit 1350 to emit light according to the content or cause of the abnormal state. In other words, the control unit 1340 generates an error signal based on the content or cause of the abnormal state, and causes the notification unit 1350 to make a notification according to the error signal. Such a configuration makes it possible for the user and/or the like to easily recognize the content or cause of a trouble that has occurred in the microphone capacitor 1331 which is a sensor for detecting the suction action.

Next, a description will be made on a series of processing in which the control unit 1340 detects that the microphone capacitor 1331 is in the abnormal state and notifies the user of the content or cause of the abnormal state. FIG. 22 is a flowchart illustrating an example of the series of processing.

The control unit 1340 determines whether the power supply button 1310 has been pressed while the aerosol generation device 1000 is in the sleep state (ST1101). When the control unit 1340 does not determine that the power supply button 1310 has been pressed (ST1101: NO), the process in step ST1101 is performed again. That is, the aerosol suction device 1000 is in the sleep state until the power supply button 1310 is pressed.

When determining that the power supply button 1310 has been pressed (ST1101: YES), the control unit 1340 causes the aerosol generation device 1000 to undergo the transition from the sleep state to the active state (ST1102).

As described above, the control unit 1340 detects whether the microphone capacitor 1331 is in the normal state or the abnormal state, based on the comparison between the voltage value applied to the PTC thermistor 1332 and the voltage threshold (ST1103).

When the voltage value applied to the PTC thermistor 1332 is equal to or higher than the voltage threshold (ST 1103: YES), that is, when it is detected that the microphone capacitor 1331 is in the abnormal state, the control unit 1340 causes the notification unit 1350 to emit light four times alternately in a warm color and a cold color, based on the control information stored in the memory unit 1350 (ST 1104).

When the voltage value applied to the PTC thermistor 1332 is lower than the voltage threshold (ST 1103: NO), the control unit 1340, as described above, determines whether the microphone capacitor 1331 is in the normal state or the abnormal state, based on whether the interval t1 between the previous suction action and the present suction action is equal to or less than the threshold time period T1 (ST105).

When the interval t1 is equal to or less than the threshold time period T1 (ST1105: YES), that is, when it is detected that the microphone capacitor 1331 is in the abnormal state, the control unit 1340 causes the notification unit 1350 to emit light six times alternately in a warm color and a cold color, based on the control information stored in the memory unit 1350 (ST1106).

When the interval t1 exceeds the threshold time period T1 (ST 1105: NO), the control unit 1340, as described above, determines whether the microphone capacitor 1331 is in the normal state or the abnormal state, based on whether the duration t2 of one suction action is equal to or less than the threshold time period T2 (ST 1107).

When the duration t2 of one suction action is equal to or less than the threshold time period T2 (ST 1107: YES), that is, when it is detected that the microphone capacitor 1331 is in the abnormal state, the control unit 1340 causes the notification unit 1350 to emit light eight times alternately in a warm color and a cold color, based on the control information stored in the memory unit 1350 (ST1108).

When the duration t2 of one suction action exceeds the threshold time period T2 (ST 1107: NO), the control unit 1340, as described above, determines whether the microphone capacitor 1331 is in the normal state or the abnormal state, based on whether the integrated heating time period t3 within the predetermined time period Ta is equal to or greater than the threshold time period T3 (ST1109).

When the integrated heating time period t3 within the predetermined time period Ta is equal to or greater than the threshold time period T3 (ST 1109: YES), that is, when it is detected that the microphone capacitor 1331 is in the abnormal state, the control unit 1340 causes the notification unit 1350 to emit light 10 times alternately in a warm color and a cold color, based on the control information stored in the memory unit 1350 (ST1110).

When the integrated heating time period t3 within the predetermined time period Ta is less than the threshold time period T3 (ST1109: NO), the control unit 1340, as described above, determines whether the microphone capacitor 1331 is in the normal state or the abnormal state, based on whether the number of times that the microphone capacitor 1331 has detected the suction action within the predetermined time period Tb is equal to or greater than N times (ST1111).

When the number of times that the microphone capacitor 1331 has detected the suction action within the predetermined time period Tb is equal to or greater than N times (ST1111: YES), that is, when it is detected that the microphone capacitor 1331 is in the abnormal state, the control unit 1340 causes the notification unit 1350 to emit light 12 times alternately in a warm color and a cold color, based on the control information stored in the memory unit 1350 (ST1112).

When the number of times that the microphone capacitor 1331 has detected the suction action within the predetermined time period Tb is less than N times (ST1111: NO), the processes of ST1103 and the subsequent steps are performed again. Accordingly, the process of determining whether the microphone capacitor 1331 is in the abnormal state is always performed while the aerosol generation device 1000 is in the active state.

Here, when the control unit 1340 detects that the microphone capacitor 1331 is in the abnormal state and causes the notification unit 1350 to emit light (ST 1104, ST 1106, ST1108, ST1110, or ST1112), the control unit 1340 causes the aerosol generation device 1000 to undergo the transition from the active state to the sleep state (ST1113). Then, the process ends.

As described above, in the aerosol generation device 1000 in the present embodiment, when detecting that the microphone capacitor 1331 which is a sensor for detecting the suction action is in the abnormal state, the control unit 1340 causes the notification unit 1350 to make a notification according to the content or cause of the abnormal state. In other words, the control unit 1340 generates an error signal based on the content or cause of the abnormal state, and causes the notification unit 1350 to make a notification according to the error signal. Such a configuration makes it possible for the user and/or the like to easily recognize the content or cause of a trouble that has occurred in the microphone capacitor 1331. In addition, according to the aerosol generation device in the present embodiment, it is unnecessary to separately perform an electrical inspection to identify the content or cause of the trouble, whereby the energy-saving effect can be achieved.

In the present embodiment, the abnormal state of the microphone capacitor 1331 is classified into five states. The control unit 1340 causes the notification unit 1360 to emit light in a different mode for each of the five states, but the configuration of the present invention is not limited thereto. That is, the number of types of error signals that can be generated by the control unit 1340 is five and the control unit 1340 causes the notification unit 1360 to emit light in a different mode for each error signal, but the configuration of the present invention is not limited thereto. For example, in each of when the interval t1 is equal to or less than the threshold time period T1 and when the duration t2 of one suction action is equal to or less than the threshold time period T2, the control unit 1340 may cause the notification unit 1350 to emit light four times alternately in a warm color and a cold color. In this case, the abnormal state of the microphone capacitor 1331 is classified into five states, and the number of the light emitting modes of the notification unit 1360 is four. As described above, in the aerosol generation device 1000 in the present embodiment, the abnormal state of the microphone capacitor 1331 is classified into n states (n is a natural number of 2 or more), and the number of types of the error signals that can be generated by the control unit 1340 (the number of the light emitting modes of the notification unit 1340) is n at the maximum. Such a configuration makes it possible to make the notification mode of the notification unit 1360 uniform for each type of the content or cause of the trouble that has occurred in the microphone capacitor 1331, which can fill the needs of the user who desires to roughly recognize the content or cause of the trouble that has occurred in the microphone capacitor 1331.

In the above-described embodiment, the description has been made assuming that the aerosol generation device 1000 generates the aerosol in response to the user's suction action, but the configuration of the present invention is not limited thereto. For example, the aerosol generation device 1000 may be configured to generate invisible vapor in response to the user's suction action. Even in such a configuration, the same effects as those of the above-described embodiment can be obtained.

In the present embodiment, the description has been made on an example in which the light is repeatedly emitted alternately in a warm color and a cold color and the number of times that the light is emitted alternately in a warm color and a cold color varies according to different light-emitting patterns, but the configuration of the present invention is not limited thereto. The notification unit may be configured to emit four type colors including a cold color, a warm color, and two medium colors (for example, yellow-green, and reddish violet) having a color tone between the cold color and the warm color so that the notification unit 1360 can emit different type colors according to the contents or causes of the above-described five abnormal states to make a notification about the content or cause of the abnormal state.

In the present embodiment, the description has been made assuming that the notification unit 1360 emits light in different modes according to the control by the control unit 1340, but the configuration of the present invention is not limited thereto. For example, the notification unit 1360 may vibrate in different modes or may emit a sound in different modes according to the contents or causes of the abnormal state of the microphone capacitor 1331 detected by the control unit 1340. Alternatively, the notification unit 1360 may make a notification by combining them. Specifically, for example, the notification unit 1360 may make a notification with a combination of light and vibration, or may make a notification with a combination of light, vibration, and sound.

In the present embodiment, when detecting that the microphone capacitor 1331 is in the abnormal state, the control unit 1340 may cause the memory unit 1350 to store the contents or causes of the abnormal state. Thereby, when detecting the user's suction action by pressing the power supply button 1310 again after the aerosol generation device 1000 undergoes the transition from the active state to the sleep state (corresponding to the above-described ST 1113), the control unit 1340 can cause the notification unit 1360 to emit light in the mode based on the content or cause of the abnormal state stored in the memory unit 1350. That is, the control unit 1350 causes the notification unit 1360 to emit light in the same mode between when detecting that the microphone capacitor 1331 is in the abnormal state and when detecting the user's suction action. Since such a configuration makes it possible to increase the opportunities to notify the user and/or the like of a trouble in the microphone capacitor 1331, the user can be surely notified of the occurrence of the trouble, and the content or cause of the trouble.

In relation to the above description, in the case where the power supply button 1310 is pressed predetermined times (for example, three times) after the aerosol generation device 1000 undergoes the transition from the active state to the sleep state (corresponding to the above-described ST1113), the control unit 1350 may cause the notification unit 1360 to emit light in the same mode as when detecting that the microphone capacitor 1331 is in the abnormal state. Such a configuration makes it possible for the user to easily recognize the occurrence of a trouble and the content or cause of the trouble by pressing the power supply button 1310 predetermined times even when any suction action cannot be detected due to the trouble in the sensor 1330, for example. In addition, since such a configuration makes it possible to increase the opportunities to notify the user and/or the like of a trouble in the microphone capacitor 1331, the user can be surely notified of the occurrence of the trouble, and the content or cause of the trouble.

Note that the control unit 1340 may cause the notification unit 1360 to emit light in the same mode as when detecting the microphone capacitor 1331 is in the abnormal state, based on an operation other than the operation of pressing the power supply button 1310 predetermined times. Specifically, for example, the control unit 1340 may cause the notification unit 1360 to emit light in the same mode as when detecting the microphone capacitor 1331 is in the abnormal state, based on the fact that the power supply part 1320 is connected to an external power supply and the charging is started. That is, the control unit 1340 may cause the notification unit 1360 to emit light in the same mode as when detecting the microphone capacitor 1331 is in the abnormal state, based on various operations that do not involve the sensor unit 1330. Such a configuration makes it possible for the user to easily recognize the occurrence of a trouble and the content or cause of the trouble even when any suction action cannot be detected due to the trouble in the sensor 1330.

In the present embodiment, the importance may be set for each of the states into which the abnormal state of the microphone capacitor 1331 is classified. For example, the importance may be set higher for the state of the microphone capacitor 1331 detected in the above-described first state detection process, and the importance may be set lower for the state of the microphone capacitor 1331 shown in FIG. 6 detected in the above-described second state detection process.

Then, the control unit 1340 may cause the notification unit 1360 to make a notification in different modes according to the importance. Specifically, for example, when detecting the abnormal state of the microphone capacitor 1331 for which the importance is set higher, the control unit 1340 may cause the notification unit 1360 to make a notification with a combination of light, vibration and sound. When detecting the abnormal state of the microphone capacitor 1331 for which the importance is set lower, the control unit 1340 may cause the notification unit 1360 to make a notification only by light, only by vibration, or only by sound. That is, when detecting the state of the microphone capacitor 1331 for which the importance is set higher, the control unit 1340 causes the notification unit 1360 to make a notification in a high power consumption mode with a combination of light, vibration and sound. In other words, the control unit 1340 generates error signals each for which the importance varying according to the state of the microphone capacitor 1331 is set, and causes the notification unit 1360 to make a notification in a different mode for each of the error signals having different importance. Note that a variety of information about the importance is stored in the memory unit 1350, for example.

Such a configuration makes it possible to make a notification not only about the content or cause of a trouble that has occurred in the microphone capacitor 1331 but also about the importance of the trouble. Furthermore, this can reduce the user's potential for overlooking the trouble with high importance that has occurred in the microphone capacitor 1331.

The present invention is not limited to the above-described embodiments as there are, but may be embodied by modifying constituent elements without departing from the gist of the invention in an implementation stage. In addition, a variety of inventions can be formed by proper combination of a plurality of constituent elements disclosed in the above-described embodiments. For example, some of all the constituent elements disclosed in the above-described embodiments may be deleted. Furthermore, the constituent elements over different embodiments may be combined with one another.

REFERENCE SIGNS LIST

1 . . . Aerosol generation device, 100 . . . Cartridge unit, 110 . . . Storage unit, 120 . . . Supply unit, 130 . . . Load, 140 . . . Atomization unit, 200 . . . Capsule unit, 210 . . . Flavor source, 300 . . . Power supply unit, 310 . . . Power supply button, 320 . . . Power supply part, 330 . . . Sensor unit, 340 . . . Control unit, 341 . . . Time measurement unit, 350 . . . Memory unit, 360 . . . Notification unit, AR . . . Air flow path, 1000 . . . Aerosol generation device, 1100 . . . Cartridge unit, 1110 . . . Storage unit, 1120 . . . Supply unit, 1130 . . . Load, 1140 . . . Atomization unit, 1200 . . . Capsule unit, 1210 . . . Flavor source, 1300 . . . Power supply unit, 1310 . . . Power supply button, 1320 . . . Power supply part, 1330 . . . Sensor unit, 1331 . . . Microphone capacitor, 1331A . . . Diaphragm, 1331B . . . Back plate, 1332 . . . PTC thermistor, 1333 . . . P-type MOSFET, 1340 . . . Control unit, 1341 . . . Time measurement unit, 1350 . . . Memory unit, 1360 . . . Notification unit, AR . . . Air flow path

The invention claimed is:

1. A power supply unit of an aerosol generation device, comprising:
   a sensor that detects an aerosol generation request while the power supply unit is in an active state;
   a control unit that determines whether the sensor is in a normal state or an abnormal state based on an output value from the sensor that has detected the aerosol generation request; and
   a memory unit,
   wherein the control unit causes the power supply unit to undergo a transition to a sleep state that allows the power supply unit to undergo a transition to the active state again when detecting the abnormal state, and
   wherein the memory unit stores information indicating the number of times that the control unit has detected the abnormal state.

2. The power supply unit of an aerosol generation device according to claim 1, wherein the control unit is capable of causing the power supply unit to undergo the transition from the sleep state to the active state again when the detected abnormal state is caused by leakage of an aerosol source.

3. The power supply unit of an aerosol generation device according to claim 1, wherein an output value from the sensor when the control unit determines that the sensor is in the normal state is different from an output value from the sensor when the control unit determines that the sensor is in the abnormal state.

4. The power supply unit of an aerosol generation device according to claim 1, wherein the output value from the sensor when the control unit determines that the sensor is in the abnormal state is a value that is not due to an aerosol generation request from a user of the aerosol generation device.

5. The power supply unit of an aerosol generation device according to claim 4, wherein the output value from the sensor when the control unit determines that the sensor is in the abnormal state is a value that is due to an aerosol generation request caused and detected by the sensor itself.

6. The power supply unit of an aerosol generation device according to claim 1, wherein the abnormal state is a state of the sensor in a case where an aerosol source is not atomized by an atomization unit that receives supply of electric power from the power supply unit or in a case where the atomization unit atomizes the aerosol source so that the aerosol source held by a supply unit that supplies the aerosol source to the atomization unit is depleted.

7. The power supply unit of an aerosol generation device according to claim 1, wherein the normal state is a state of the sensor in a case where an atomization unit that receives supply of electric power from the power supply unit atomizes an aerosol source so that the aerosol source held by a supply unit that supplies the aerosol source to the atomization unit is not depleted.

8. The power supply unit of an aerosol generation device according to claim 1, wherein the control unit determines that the sensor is in the abnormal state when a time interval from when the sensor detects a certain aerosol generation request to when the sensor detects a next aerosol generation request is equal to or less than a predetermined threshold.

9. The power supply unit of an aerosol generation device according to claim 1, wherein the control unit determines that the sensor is in the abnormal state when duration of an aerosol generation request detected by the sensor is equal to or less than a predetermined threshold.

10. The power supply unit of an aerosol generation device according to claim 1, wherein the control unit determines that the sensor is in the abnormal state when a total time period for which the sensor detects an aerosol generation request within a predetermined time period is equal to or greater than a predetermined threshold.

11. The power supply unit of an aerosol generation device according to claim 1, wherein the control unit determines that the sensor is in the abnormal state when the number of times that the sensor has detected an aerosol generation request within a predetermined time period is equal to or greater than a predetermined threshold.

12. The power supply unit of an aerosol generation device according to claim 1, further comprising:
a notification unit,
wherein when determining that the sensor is in the abnormal state, the control unit causes the notification unit to make a notification that the sensor is in the abnormal state.

13. The power supply unit of an aerosol generation device according to claim 1, wherein the memory unit further stores information indicating a content of the abnormal state detected by the control unit.

14. The power supply unit of an aerosol generation device according to claim 1, wherein when detecting an instruction to cause the power supply unit to undergo a transition to an active state, the control unit does not cause the power supply unit to undergo the transition to the active state when the number of times that the control unit has detected the abnormal state is equal to or greater than a predetermined threshold, or causes the power supply unit to undergo the transition to the active state when the number of times is less than the predetermined threshold.

15. The power supply unit of an aerosol generation device according to claim 1, wherein the control unit performs a process of detecting whether the sensor is in the normal state or the abnormal state while the power supply unit is in the active state.

16. A control method for a power supply unit of an aerosol generation device, comprising:
determining whether a sensor is in a normal state or an abnormal state based on an output value from the sensor that has detected an aerosol generation request while the power supply unit is in an active state; and
causing the power supply unit to undergo a transition to a sleep state that allows the power supply unit to undergo a transition to the active state again, when detecting the abnormal state,
wherein information is stored in a memory unit indicating the number of times that the control unit has detected the abnormal state.

* * * * *